US007927629B2

(12) United States Patent
Simone et al.

(10) Patent No.: US 7,927,629 B2
(45) Date of Patent: Apr. 19, 2011

(54) METHOD AND COMPOSITIONS FOR POLYMER NANOCARRIERS CONTAINING THERAPEUTIC MOLECULES

(75) Inventors: Eric Simone, Philadelphia, PA (US); Vladimir R. Muzykantov, Warwick, PA (US); Thomas D. Dziubla, Lexington, KY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 467 days.

(21) Appl. No.: 11/925,834

(22) Filed: Oct. 27, 2007

(65) Prior Publication Data

US 2009/0110741 A1 Apr. 30, 2009

(51) Int. Cl.
*A61K 9/16* (2006.01)
*A61K 9/50* (2006.01)
*A61K 38/00* (2006.01)
*A61K 38/54* (2006.01)

(52) U.S. Cl. .......... 424/497; 424/499; 424/93.3; 514/12

(58) Field of Classification Search ........................ None
See application file for complete search history.

(56) References Cited

U.S. PATENT DOCUMENTS

| | | | | |
|---|---|---|---|---|
| 5,543,158 | A | 8/1996 | Gref et al. | |
| 5,866,540 | A | 2/1999 | Jonczyk et al. | |
| 6,007,845 | A * | 12/1999 | Domb et al. | 424/501 |
| 7,597,907 | B2 | 10/2009 | Muzykantov | |
| 2004/0001872 | A1 | 1/2004 | Shih et al. | |
| 2004/0208929 | A1 | 10/2004 | Costantino | |
| 2006/0073333 | A1 | 4/2006 | Anderson | |
| 2006/0127386 | A1 | 6/2006 | Muzykantov et al. | |
| 2009/0258078 | A1 | 10/2009 | Muzykantov | |

FOREIGN PATENT DOCUMENTS

WO WO98/32466 7/1998

OTHER PUBLICATIONS

Dziubla, J. Cont. Rel., 102, 2005.*
Ya-Ping, J. Cont. Rel., 71, 2001.*
Geng, Polymer, 47, 2006.*

(Continued)

*Primary Examiner* — Robert A Wax
*Assistant Examiner* — William Craigo
(74) *Attorney, Agent, or Firm* — Howson & Howson LLP

(57) ABSTRACT

A method of controlling a physical characteristic of polymeric nanocarrier-encapsulated protein particles includes altering or selecting a weight percentage of a hydrophobic polymer block in a total amphiphilic diblock copolymer of a primary emulsion of a double emulsion, freeze-thaw technique. The primary emulsion is formed using a freeze-thaw cycle of the amphiphilic diblock copolymer and a protein having a molecular weight of up to or equal to 300,000 Da. Selection of the hydrophobic polymer block percentage alters one or more characteristics of the resulting nanoparticles, such as shape. Thus, as one aspect, a method of producing filamentous polymeric nanocarrier-encapsulated protein (i.e., active enzyme) particles involves forming a primary emulsion using a freeze-thaw cycle of (i) an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer comprises greater than 81% to about 95% by weight of the hydrophobic polymer block; and a protein having a molecular weight of up to or equal to about 300,000 Da. Various compositions comprising such filamentous-shaped nanocarrier particles, and methods of use for diagnosis and therapy are disclosed.

17 Claims, 8 Drawing Sheets

OTHER PUBLICATIONS

Geng, JACS, 127, 2005.*

Muzykantov, V. R., "Targeting of superoxide dismutase and catalase to vascular endothelium", J. Control Release, 71(1): 1-21 (Mar. 12, 2001).

Langer, R., "Drug Delivery and Targeting", Nature, 392(6679 Suppl):5-10 (Apr. 30, 1998).

Moghimi, et al., "Stealth Liposomes and Long Circulating Nanoparticles: Critical issues in pharmacokinetics, opsonization and protein-binding properties", Prog. Lipid Res., 42(6):463-478 (Nov. 2003).

Roux, et al., "On the characterization of pH sensitive liposome/polymer complexes", Biomacromolecules, 4(2):240-248 (Mar.-Apr. 2003).

Lasic, D. D., "Doxorubicin in sterically stabilized lysosomes", Nature, 380(6574):561 (Apr. 11, 1996).

Discher, et al, "Polymer vesicles", Science, 297(5583):967-973 (Aug. 9, 2002).

Zhang, et al., Micellization Phenomena of Amphiphilic Block Copolymers Based on Methoxy Poly(ethylene glycol) and Either Crystalline or Amorphous Poly(caprolactone-b-lactide) Biomacromolecules, 7(9):2492-2500 (Sep. 2006).

Vinogradov, et al., "Self-Assembly of Polyamine-Poly(ethylene glycol) Copolymers with Phosphorothioate Oligonucleotides" Bioconjug. Chem., 9(6):805-812 (Nov.-Dec. 1998).

Ravenelle, et al., "Self-Assembly of Poly([R]-3-hydroxybutyric acid)-Block-Poly(ethylene glycol) Diblock Copolymers" Biomacromolecules, 4(3):856-858 (May-Jun. 2003).

Zhang, et al., "Multiple morphologies of "crew cut" aggregates of polystyrene-b-poly(acrylic acid) block copolymers", Science, 268(5218):1728-1731 (Jun. 23, 1995).

Alakhov, et al., "Block copolymeric transport carriers as versatile vehicles for drug delivery", Expert Opin. Investig. Drugs, 7(9):1453-1473 (Sep. 1998).

Dziubla, et al., "Polymer nanocarriers protecting enzyme cargo against proteolysis", J. Control Release, 102(2):427-439 (Feb. 2, 2005 ; e-pub Nov. 19, 2004).

Christofidou-Solomidou, et al., "PECAM-directed delivery of catalase to endothelium protects against pulmonary vascular oxidative stress", Am. J. Physiol. Lung Cell Mol. Physiol., 285(2):L283-L292 (Aug. 2003).

Kozower, et al., "Immunotargeting catalase to the pulmonary endothelium alleviates oxidative stress and reduces acute lung transplantation injury" Nat. Biotechnol., 21(4):392-398 (Apr. 2003 ; e-pub Mar. 24, 2003).

Muro, et al., "Slow intracellular trafficking of catalase nanoparticles targeted to ICAM-1 protects endothelial cells from oxidative stress" Am. J. Physiol. Cell Physiol., 285(5):C1339-C1347 (Nov. 2003 ; e-pub Jul. 23, 2003).

Champion, et al., "Role of target geometry in phagocytosis" Proc. Natl. Acad. Sci. USA., 103(13):4930-4934 (Mar. 28, 2006 ; e-pub Mar. 20, 2006).

Son, et al., "Template synthesis of multifunctional nanotubes for controlled release" J. Control Release, 114(2):143-152 (Aug. 28, 2006 ; e-pub Jun. 7, 2006).

Cai, et al., "Micelles of different morphology: advantages of worm-like filomicelles of PEO-PCL in paclitaxel delivery" Pharm. Res., 24:2099-2109 (Nov. 2007 ; e-pub Jun. 13, 2007).

Geng, et al., "Shape effects of filaments versus spherical particles in flow and drug delivery" Nat. Nano., 2(4):249-255 (Mar. 25, 2007).

Geng, et al., "Visualization of degradable worm micelle breakdown in relation to drug release" Polymer, 47(7):2519-2525 (Feb. 7, 2006).

Shuvaev, et al., "Factors modulating the delivery and effect of enzymatic cargo conjugated with antibodies targeted to the pulmonary endothelium", J. Control. Release, 118(2):235-244 (Apr. 2, 2007 ; e-pub Jan. 8, 2007).

Von Burkersroda, et al., "Why degradable polymers undergo surface erosion or bulk erosion", Biomaterials, 23(21):4221-4231 (Nov. 2002).

Gopferich, A., "Polymer Bulk Erosion" Macromolecules, 30(9):2598-2604 (Apr. 1, 1997).

Simone, et al., "Effect of Polymer Amphiphilicity on Loading of a Therapeutic Enzyme into Protective Filamentous and Spherical Polymer Nanocarriers" Biomacromolecules, 8(12):3914-3921 (Dec. 2007 ; e-pub Nov. 27, 2007).

Dziubla, et al., "Endothelial targeting of semi-permeable polymer nanocarriers for enzyme therapies" Biomaterials, 29(2):215-227 (Jan. 2008 ; e-pub Oct. 24, 2007).

Muzykantov, et al., "Immunotargeting of antioxidant enxymes to the pulmonary endothelium", Proc. Natl. Acad. Sci. USA, 96(5):5213-5218 (May 1996).

Atochina, et al., "Immunotargeting of catalase to ACE or ICAM-1 protects perfused rat lungs against oxidative stress", Am. J. Physiol., 275 (Lung Cell. Mol. Physiol. 19):L806-L817 (Oct. 1998).

Avgoustakis, et al., "PGLA-mPEG particles of cisplatin: in vitro nanoparticle degredation, in vitro drug release and in vitro drug residence in blood properties", J. Control. Release, 79:123-135 (Feb. 19, 2002).

Hansen, et al. "Attachment of antibodies to sterically stablized liposomes: evaluation, comparison and optimization of coupling procedures", Biochimica et Biophysica Acta, 1239:133-144 (Nov. 1, 1995).

Zambaux, et al., "Protein-C loaded monomethoxypoly (ethylene oxide)-poly(lactic acid) nanoparticles", Int'l. J. Pharmaceutics, 212:1-9 (Jan. 5, 2001).

McCord, J.M., "Superoxide dismutase on aging and disease: an overview", Methods in Enzymology, 349:331-341 (2002).

Wu, et al., "Neuroprotection with noninvasive neurotrophin deliver to the brain", Proc. Natl. Acad. Sci. USA, 96:254-259 (Jan. 5, 1999).

Sweitzer, et al., "PECAM directed immunotargeting of catalase: specific, rapid and transient protection against hydrogen peroxide", Free Radical Biology & Medicine, 34(8):1035-1046 (Apr. 15, 2003).

Wiewrodt, et al., "Size-dependent intracellular immunotargeting of therapeutic cargoes into endothelial cells", Hemostasis, Thrombosis, and Vascular Biology, 99(3):912-922 (Feb. 1, 2002).

Garnacho, et al., "Delivery of acid sphingomyelinase in normal and Niemann-Pick disease mice using ICAM-1-targeted polymer nanocarriers", J. Pharmacol. Exp. Ther. (e-pub Feb. 20, 2008).

Ahmed et al, "Self-porating polymersomes of PEG-PLA and PEG-PCL: hydrolysis-triggerted controlled release vesicles", J. Controlled Release, vol. 96, p. 37-53, (2004).

Muzykantov et al, "Streptavidin facilitates internalization and pulmonary targeting of an anti-endothelial cell antibody (platelet-endothelial cell adhesion molecule 1): a strategy for vascular immunotargeting of drugs", Proceedings of the National Academy of Sciences USA, 96(5):2379-2384 (Mar. 1999).

Office Action dated Aug. 14, 2008 from U.S. Appl. No. 11/266,785.

Amendment dated Nov. 14, 2008 from U.S. Appl. No. 11/266,785.

Examiner's Amendment with Notice of Allowance dated Mar. 6, 2009 in U.S. Appl. No. 11/266,785.

International Search Report dated Dec. 8, 2008 issued in International Patent Application No. PCT/US2008/081331.

International Preliminary Report on Patentability dated May 6, 2010 issued in International Patent Application No. PCT/US2008/081331.

* cited by examiner

FIG. 1A
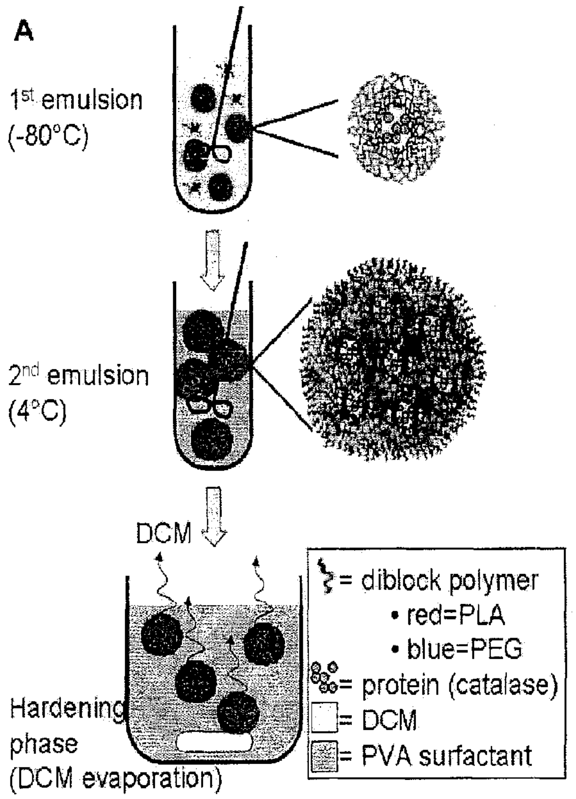
FIG. 1B
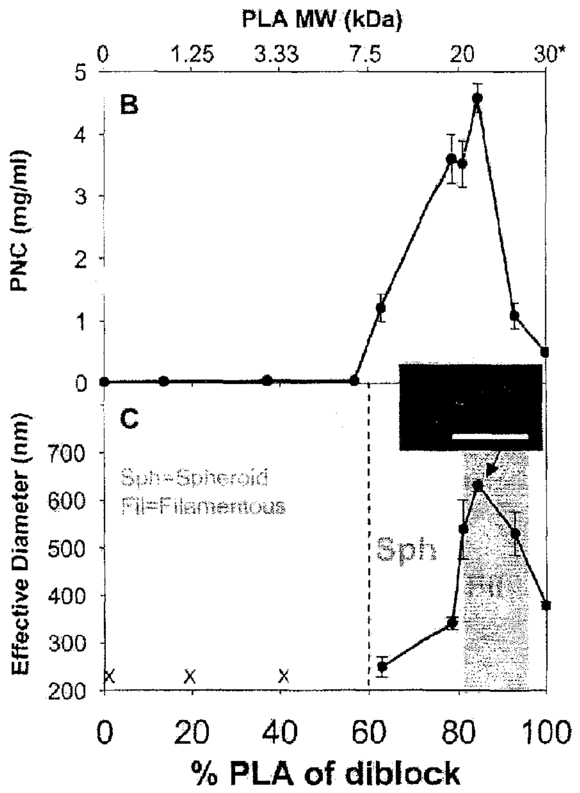
FIG. 1C

METHOD AND COMPOSITIONS FOR POLYMER NANOCARRIERS CONTAINING THERAPEUTIC MOLECULES

STATEMENT REGARDING FEDERALLY SPONSORED RESEARCH OR DEVELOPMENT

The present invention was supported by Grant Nos. HL007954, HL073940-01-A1, PO1-HL079063 from the National Institutes of Health. The government has an interest in the invention.

BACKGROUND OF THE INVENTION

Rapid clearance from the circulation, inactivation by proteases and inhibitors, and a lack of affinity for the desired target sites of action limit the utility of potent but labile therapeutic proteins (Muzykantov, V. R., *J Control Release* 2001, 71, (1), 1-21). Diverse drug delivery systems (e.g., natural lipoproteins, liposomes and polymer nanocarriers) are being widely designed in order to maximize drug efficacy and minimize side effects (Langer, R., *Nature* 1998, 392, (6679 Suppl), 5-10). For example, polyethylene glycol (PEG), a hydrophilic polymer that enhances aqueous solubility, masks drugs and carriers from host defense systems and prolongs circulation in the bloodstream ("stealth" technology) (Moghimi, S. M. et al, *Prog Lipid Res* 2003, 42, (6), 463-78; Roux, E. et al, *Biomacromolecules* 2003, 4, (2), 240-248). Nanocarriers coated with PEG are already in clinical use for the intravascular delivery of anti-tumor agents, in the form of stealth liposomes (e.g., Doxil®) (Lasic, D. D., *Nature* 1996, 380, (6574), 561).

Comparatively little success has been achieved, however, in nanocarrier mediated delivery of therapeutic proteins, which is especially challenging because protein's biological activity requires maintaining it's native folded state. Loading therapeutic proteins into biodegradable polymer nanocarriers (PNC) can be complicated by protein unfolding and inactivation. Loss of enzymatic activity due to protein unfolding in harsh conditions of PNC formulation has represented a major barrier to the use of biodegradable co-polymers for delivery of therapeutic enzymes.

Formulations based on synthetic amphiphilic copolymers that consist of hydrophobic blocks conjugated with hydrophilic PEG blocks yield a variety of aggregate shapes, namely micelles, vesicles and frozen particles—a versatile palette of polymer nanocarriers with further diversity in size and degradation patterns (Discher, D. E. et al, *Science* 2002, 297, (5583), 967-73; Zhang, J. et al., *Biomacromolecules* 2006, 7, (9), 2492-2500; Vinogradov, S. V., et al, *Bioconjug Chem* 1998, 9, (6), 805-12; Discher, D. E. et al, 2002, cited above; Ravenelle, F. et al, *Biomacromolecules* 2003, 4, (3), 856-858; Zhang, L.; Eisenberg, A., *Science* 1995, 268, (5218), 1728-1731; and Alakhov, V. Y. et al, *Expert Opin Investig Drugs* 1998, 7, (9), 1453-73). However, encapsulation of large therapeutic proteins, especially enzymes, without loss of their biological activity into these polymer nanoparticles formed by self-assembly mechanism has not been reported, because conditions providing their formulation via this mechanism are not compatible with retaining enzymatic activity.

A relatively mild freeze-thaw double emulsion method for the encapsulation of active catalase, a large 249 kDa tetrameric enzyme, into PEG-PL(G)A (poly lactic-co-glycolic acid) PNC is discussed in US Patent Application Publication No. 2006/0127386. PLGA is a biodegradable FDA-approved co-polymer used for the production of drug delivery systems and sutures. Furthermore, $H_2O_2$, a reactive oxygen species widely implicated in the pathogenesis of many disease conditions (Muzykantov 2001, cited above) is freely diffusible through PL(G)A (Dziubla, T. D.; et al, *J Control Release* 2005, 102, (2), 427-39). Catalase encapsulated within PEG-PL(G)A PNC as discussed in the preceding three publications was protected from proteolysis and decomposed $H_2O_2$ diffusing through the PNC shell. The freeze thaw cycle added during the primary emulsion enhanced catalase loading into PNC and reduced its formulation-induced inactivation.

Despite the specificity of therapeutic enzymes, medical utility is often limited by inadequate delivery and insufficient stability in the body. For example, catalase is a naturally occurring antioxidant enzyme that can be used for the treatment of vascular oxidative stress involved in the pathogenesis of many disease conditions (Muzykantov 2001, cited above). However, catalase and other antioxidant enzymes (e.g., superoxide dismutase) have no practical medical utility due to inadequate delivery to therapeutic sites, especially the endothelial cells lining the luminal surface of blood vessels. Conjugation of enzymes to targeting antibodies improves delivery and effects of antioxidant enzymes in diverse animal models (Christofidou-Solomidou, M. et al, *Am J Physiol Lung Cell Mol Physiol* 2003, 285, (2), L283-92; Kozower, B. D. et al, *Nat Biotechnol* 2003, 21, (4), 392-8), and yet therapeutic duration is limited to a few hours by catalase proteolysis at the target site (Muro, S. et al, *Am J Physiol Cell Physiol* 2003, 285, (5), C1339-47).

There remains a need in the art for improved compositions and methods for targeting active therapeutic proteins to cells which maintains folded and active protein, provides protection of the encapsulated proteins from subsequent proteolysis degradation, and prolongs their biological activity in vivo.

SUMMARY OF THE INVENTION

In one aspect, a method of controlling a physical characteristic of polymeric nanocarrier particles containing encapsulated biologically active protein (i.e., polymeric nanocarrier-encapsulated protein particles) is disclosed. The method includes altering or selecting a weight percentage of a hydrophobic polymer block in a total amphiphilic diblock copolymer of a primary emulsion. The primary emulsion is formed using a freeze-thaw cycle of: (i) the amphiphilic diblock copolymer, which has a molecular weight of about 10,000 to about 100,000 Da and is a conjugate of the hydrophobic polymer block and a hydrophilic polymer block; and (ii) a biologically active protein having a molecular weight of up to or equal to 300,000 Da. A secondary emulsion is formed from the primary emulsion. The particles having the selected characteristics are recovered from this method. According to this method, the size and shape of the protein-polymer composition and protection of the protein against external proteolysis and mechanism of degradation of the nanocarriers are controlled by the weight percentage of the hydrophobic polymer block in the total amphiphilic diblock copolymer. Thus, in one embodiment, the weight percentage of hydrophobic polymer block in a total amphiphilic diblock copolymer of the primary emulsion is about 60% to less than 80% by weight of the hydrophobic polymer block, resulting in polymeric nanocarrier-encapsulated protein particles of primarily spherical shape. In another embodiment, the weight percentage of hydrophobic polymer block in a total amphiphilic diblock copolymer of the primary emulsion is from 80% to less than 81% by weight of the hydrophobic polymer block, resulting in a mixture of spherical and filamentous shapes of polymeric nanocarrier-encapsulated protein particles.

In another aspect, a method of producing primarily filamentous polymeric nanocarrier-encapsulated protein particles includes forming a primary emulsion using a freeze-thaw cycle of (i) an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer contains greater than 81% to about 95% by weight of the hydrophobic polymer block; and (ii) a protein having a molecular weight of up to or equal to about 300,000 Da. A secondary emulsion is formed from the primary emulsion. Recovery of primarily filamentous particles is permitted by this method.

In another aspect, a composition of polymeric nanocarrier-encapsulated protein particles is provided. The compositions contains (a) a protein having a molecular weight of up to or equal to about 300,000 Da; (b) an amphiphilic diblock copolymer having a molecular weight of about 10,000 to about 100,000 Da and which is a conjugate of a hydrophilic polymer block and a hydrophobic polymer block, wherein the total amphiphilic diblock copolymer is greater than about 80% by weight of the hydrophobic polymer block. This composition contains filamentous-shaped nanocarrier particles. In one embodiment, wherein the total amphiphilic diblock copolymer comprises between 80-81% by weight of the hydrophobic polymer block, the composition comprises a mixture of spherical shaped particles and filamentous particles. In another embodiment, wherein the total amphiphilic diblock copolymer comprises between 82 to 95% by weight of the hydrophobic polymer block, the composition comprises primarily filamentous particles.

In still another aspect, a pharmaceutical composition contains the filamentous polymeric nanocarrier-encapsulated protein particles in which the encapsulated protein is a therapeutically useful protein with retained biological activity. In one such embodiment, such a protein is a therapeutically useful enzyme. In yet another embodiment, the substrate for the encapsulated enzyme is freely diffusible through the polymer material of the nanoparticles, which permits prolonged enzymatic activity by the polymeric nanocarrier-encapsulated protein particles protecting protein from proteolysis.

In another aspect, a drug delivery vehicle comprises the filamentous polymeric nanocarrier-encapsulated protein particles of this invention.

In still another aspect, a pharmaceutical composition comprises the mixed spherical/filamentous polymeric nanocarrier-encapsulated protein particles in which the encapsulated protein is a therapeutically useful protein. In one such embodiment, such a protein is a therapeutically useful, biologically active enzyme.

In another aspect, a composition of polymeric nanocarrier-encapsulated protein particles is provided, which comprises (a) a biologically active protein having a molecular weight of up to or equal to about 300,000 Da; (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises about 60 to 80% by weight of the hydrophobic polymer block. This composition comprises spherical particles with diameters of about 250 to 350 nm.

In still another aspect, a pharmaceutical composition comprises the spherical polymeric nanocarrier-encapsulated protein particles in which the encapsulated protein is a therapeutically useful protein. In one such embodiment, such a protein is a therapeutically useful enzyme.

In another aspect, the protein employed in the composition or the particule itself comprises an affinity moiety on its outer surface, such as an antibody, or a fragment of such an antibody, directed to a specific surface determinant on a target cells. In still another aspect, the protein/particles in the composition have affinity moieties on the outer surfaces thereof, such as an antibody or a fragment of such an antibody, directed to a cell adhesion molecule.

In yet a further aspect, a diagnostic or therapeutic method is provided which comprises administering to a mammalian subject or tissue thereof in vivo, ex vivo or in vitro, one of the pharmaceutical compositions described above.

In another aspect, a diagnostic or therapeutic method is described comprising administering to a mammalian subject or tissue thereof in vivo, ex vivo or in vitro, a composition or particle produced by any of the methods described herein. These compositions are preferably produced by a double emulsion formulation without inactivation of the encapsulated protein.

Other aspects and advantages are provided in the following detailed description.

BRIEF DESCRIPTION OF THE FIGURES

FIG. 1A is a schematic of freeze thaw-emulsion formulated polymeric nanocarriers (PNC) showing that PNC yield and effective size depend on the molecular weight percentage of the hydrophobic block polymer (e.g., polylactic acid) in the amphiphilic diblock copolymer (also containing a hydrophilic block polymer).

FIG. 1B is a graph showing that mass yield of PNC was determined by either the hydrophilic block polymer (e.g., polyethylene glycol; PEG) or the hydrophobic block polymer (e.g., PLA) content and all particle preparations were resuspended in 1 ml phosphate buffered saline (PBS).

FIG. 1C is a graph showing that sizing was determined by dynamic light scattering (DLS). "Sph" indicates the spheroid PNC range, while "Fil" notes the filamentous PNC range. Shades of gray denote PLA percent providing formulation of spherical (white), filamentous (gray) and mixed (light grey) geometries of PNC. Inset shows confocal fluorescent microscopy image of filamentous 84% PLA PNC. Staining was performed with the lipophilic carbocyanine dye, PKH26, intercalated into the PNC polymer. Scale bar is 5 μm. Data are shown as mean value±standard deviation.

FIG. 2A shows a spherical copolymer of mPEG (5K) and PLA (8.5K) at 63% PLA. FIG. 2B shows a spherical copolymer of mPEG (5K) and PLA (18K) at 78.5% PLA. FIG. 2C shows a mixed spherical/filamentous population of a copolymer of mPEG (5K) and PLA (21K) at 81% PLA. FIG. 2D shows a filamentous copolymer of mPEG (5K) and PLA (27K) at 84% PLA. FIG. 2E shows a filamentous copolymer of mPEG (5K) and PLA (64K) at 93% PLA. A transition from spherical (60-79 wt % of the hydrophobic polymer block, e.g., PLA) to mixed populations (80-81% PLA) to filamentous structures (>81-95% PLA) is seen with increasing PLA content measured by weight percentage of the total amphiphilic diblock copolymer. Scale bar is 500 nm.

FIG. 3A is a graph showing that loading by mass is defined as protein mass in PNC divided by the total amount added to the particle preparation during the freeze-thaw modified double emulsion formulation. FIG. 3B is a graph showing that enzyme inactivation increased at the higher ranges of PLA % in the formulation. FIG. 3C is a graph showing enzymatic activity of catalase lost during the formulation homogenizations, based on kinetics of $H_2O_2$ degradation. Percent of activity of total protein mass added is shown. The greatest enzyme protection from formulation occurs between 63 and 84 wt % of the hydrophobic block polymer, e.g., PLA. Loading of catalase into mPEG-PLA PNC was based on enzymatic activity. For all figures, MW region with % PLA <60% was omitted due to negligible PNC content by polymer mass.

FIG. 4A shows that activity of free catalase is practically eradicated after 1 hour of incubation with pronase. Activity of PNC-loaded catalase decreases by ~70% after five hours of incubation and stabilizes afterwards. Inset illustrates the concept of a PNC "protective cage" which is impermeable to proteases, yet freely permeable to the encapsulated enzyme substrate, $H_2O_2$. FIG. 4B is a graph showing diverse % PLA PNC loaded with $^{125}$I-catalase were incubated with pronase for 1 hr and degraded protein was separated from protected/encapsulated protein by centrifugation. This measure has been shown to correlate linearly with preservation of enzymatic activity.

FIGS. 6A and 6B show degradation at pH 7.4 and pH 2.5, respectively, on Day 0. FIGS. 6C and 6D show degradation at pH 7.4 and pH 2.5, respectively, on Day 7. FIGS. 6E and 6F show degradation at pH 7.4 and pH 2.5, respectively, on Day 14. FIGS. 6G and 6H show degradation at pH 7.4 and pH 2.5, respectively, on Day 21. Morphology changes of (87% PLA) filamentous PNC by TEM over 1 month degradation in neutral and acidic pH are shown. Filamentous PNC show higher sensitivity at pH 2.5 (FIGS. 6B, 6D, 6F and 6H) while no morphologic change is evident at neutral pH (FIGS. 6A, 6C, 6E and 6G). Similar trends for filamentous PNC composed of PEG copolymer with higher PLA MW were observed (see FIG. 7). Scale bar is 500 nm.

FIGS. 8A and 8B show condition of the PNC on Day 0 at pH 2.5 and 7.4, respectively. FIGS. 8A and 8D show condition of the PNC on Day 7 at pH 2.5 and 7.4, respectively. FIGS. 8E and 8F show condition of the PNC on Day 14 at pH 2.5 and 7.4, respectively. FIGS. 8G and 8H show condition of the PNC on Day 21 at pH 2.5 and 7.4, respectively. Higher MW (93% PLA) filamentous PNC show slightly higher resistance to degradation than lower MW filamentous PNC at low pH, as demonstrated through slower transition to vesicles over time. Overall, trends are similar to lower MW filamentous PNC with no change at neutral pH and a transition to shorter filaments and vesicles at acidic pH. Scale bar is 500 nm.

DETAILED DESCRIPTION OF THE INVENTION

Figures 2A, 2B, 2C, 2D, 2E:
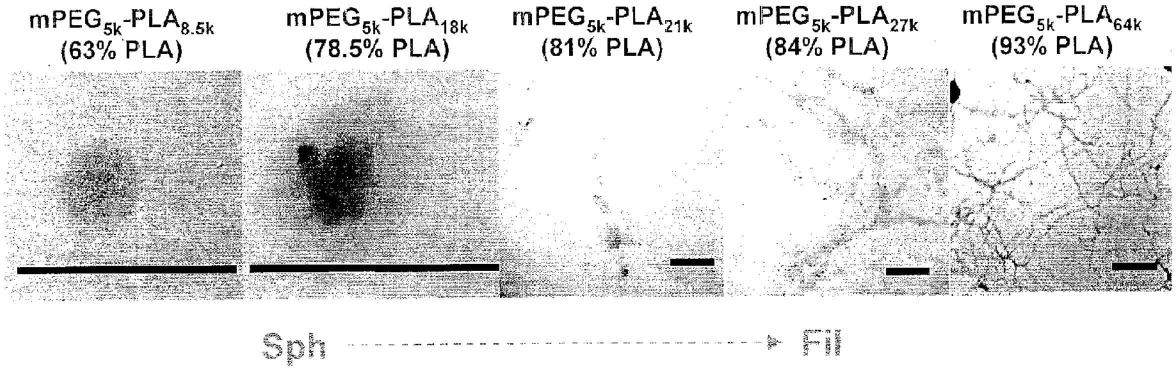
FIGS. 2A-2E are photomicrographs showing that amphiphilicity of an exemplary diblock PEG-PLA copolymer controls PNC morphology. Morphologic images are obtained by transmission electron microscopy (TEM) with uranyl acetate staining.

The above-stated needs in the art are met by the following described compositions and methods for novel delivery systems that can accommodate large molecular weight therapeutic and diagnostic proteins. The following compositions and methods are based upon the inventors' discovery that for polymeric nanocarriers (PNC) composed of a hydrophobic polymer block and a hydrophilic polymer block, the percentage by weight of the hydrophobic polymer block to the total weight of the diblock copolymer is a key parameter that governs PNC assembly, geometry and stability, as well as enzyme loading, activity and subsequent protection against proteolysis. Through control of molecular weight composition, the methods and compositions described herein can, in one embodiment, produce filamentous carriers containing biologically active enzyme cargo that is protected from proteolysis. By balancing the amphiphilic character of the PNC, the methods and compositions provide a nanocarrier well suited for the prolonged delivery of enzymes and other proteins.

Thus, in one aspect, a method of controlling a physical characteristic of polymeric nanocarrier-encapsulated protein particles involves altering or selecting a weight percentage of a hydrophobic polymer block in a total amphiphilic diblock copolymer used in a freeze-thaw modified double emulsion method of forming a polymeric nanocarrier (PNC). Embodiments of suitable double emulsion methods are described in Dziubla, T. D.; et al, *J Control Release* 2005, 102, (2), 427-39 and U.S. Patent Application Publication No. 2006/0127386, incorporated herein by reference. The homogenization in the double emulsion formulation produces PNC of desired size (200-500 nm), yet also reduces enzyme activity and decreases loading of the enzyme drug. The freeze-thaw cycle aids synthesis of enzyme-loaded PNC by both enhancing the amount of loaded enzyme and protecting it from inactivation (Dziubla et al 2005, cited above).

The method involves the steps of homogenizing or mixing at least one protein and the amphiphilic diblock copolymer solution (an aqueous phase) at subzero temperature so that a primary emulsion is formed. The amphiphilic diblock copolymer is mixed or homogenized with aqueous solutions of the protein by methods including, but not limited to, mechanical or ultrasound homogenization or pressure homogenization. A secondary emulsion is formed generally by mixing or homogenizing the primary emulsion with a surfactant. The nanoparticles having the requisite physical characteristics are recovered therefrom, generally following one or more centrifugations. The inventors have discovered that a physical characteristic such as one or more of: the size of the polymeric nanocarrier-encapsulated protein particles, the shape of the polymeric nanocarrier-encapsulated protein particles, the protection of the protein against external proteolysis, and the mechanism of degradation of the polymeric nanocarrier-encapsulated protein particles can be desirably generated in such a method when the actual weight % of the hydrophobic polymer block $\overline{M_n}$ to the entire diblock copolymer $\overline{M_n}$ is adjusted as discussed herein.

As supported in the examples below, the inventors encapsulated an exemplary active enzyme into an exemplary amphiphilic diblock copolymer (e.g., methoxy-poly(ethylene glycol-block-lactic acid) (mPEG-PLA) PNC, with a freeze-thaw double emulsion technique as described by Dziubla, et al, 2005, cited above. Using concepts of spontaneous curvature, the inventors hypothesized that the copolymer block ratio would influence PNC morphology and loading and examined PNC yield, shape, stability, loading, activity and protease resistance of the exemplary antioxidant enzyme, catalase. It was surprisingly discovered that PNC transitioned from spherical to filamentous shapes with increasing hydrophobic polymer fraction. Importantly, the inventors demonstrated for the first time encapsulation of an active therapeutic enzyme into filamentous carriers. As noted in the examples below, a PNC produced as described herein using a diblock copolymer formed filamentous particles loaded with significant levels of protease-resistant enzyme. The inventors further determined that PNC morphology also greatly influenced its degradation, offering a new means of controlled delivery.

The methods described herein use varying polymer MW and amphiphilicity in the freeze thaw synthesis of PNC to develop desirable PNC compositions loaded with protein. With constant hydrophilic polymer block (e.g., PEG) content, the MW of the hydrophobic polymer block (e.g., PLA) in the diblock copolymer determines the overall amphiphilicity.

Thus, in such a method the primary emulsion is formed using a freeze-thaw cycle of an amphiphilic diblock copolymer, which has a molecular weight of about 10,000 to about 100,000 Da and comprises a conjugate of the hydrophobic polymer block and a hydrophilic polymer block, and a protein having a molecular weight of up to or equal to 300,000 Da. In one embodiment, when a weight percentage of hydrophobic polymer block in a total amphiphilic diblock copolymer of the primary emulsion is about 60% to less than 80% by weight of the hydrophobic polymer block in this method, polymeric nanocarrier-encapsulated protein particles are produced having a substantially or primarily spherical shape. The method produces spherical nanoparticles having diameters of about 250 to 350 nm. Thus, in certain embodiments, the spherical nanoparticles produced by this method have a diameter of at least 250, 260, 270, 280, 290, 300, 310, 320, 330, 340 or 350 nm.

In another embodiment, when a weight percentage of hydrophobic polymer block in a total amphiphilic diblock copolymer of the primary emulsion is from 80% to less than 81% by weight of the hydrophobic polymer block, the polymeric nanocarrier-encapsulated protein particles are produced having a mixture of spherical and filamentous shapes.

In yet another embodiment, a method of producing filamentous polymeric nanocarrier-encapsulated protein particles is disclosed herein. According to this method, a primary emulsion is formed using a freeze-thaw cycle of an amphiphilic diblock copolymer, which has a molecular weight of about 10,000 to about 100,000 Da and comprises a conjugate of the hydrophobic polymer block and a hydrophilic polymer block, wherein the amphiphilic diblock copolymer comprises greater than 81% to about 95% by weight of the hydrophobic polymer block; and a protein having a molecular weight of up to or equal to about 300,000 Da. A secondary emulsion is formed from the primary emulsion. The method also includes recovering polymeric nanocarrier-encapsulated protein particles having a primarily filamentous shape from this method. Filamentous nanoparticles produced by this method have a diameter of less than 70 nm. In one embodiment, such filamentous particles have a diameter of 30-60 nm, dependent on the copolymer MW. In other embodiments, the particles have a diameter of at least 60 nm, 50 nm, 40 nm, 30 nm or lower. Such filamentous nanoparticles also have a length of from about 1 to about 50 microns. Thus, in certain embodiments, the filamentous nanoparticles produced herein have lengths of at least 2, 5, 10, 15, 20, 25, 30, 35, 40, 45 or 50 microns in length.

All of the methods described above may further include an additional method step of conjugating an affinity moiety to the surface of the polymeric nanocarrier-encapsulated protein particles.

Thus, in another aspect, a composition is provided that comprises polymeric nanocarrier-encapsulated protein particles comprising (a) a protein having a molecular weight of up to or equal to about 300,000 Da; (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises greater than about 80% by weight of the hydrophobic polymer block. This composition comprises filamentous-shaped nanocarrier particles. In one embodiment of this composition in which the total amphiphilic diblock copolymer comprises between 80-81% by weight of the hydrophobic polymer block, the composition comprises a mixture of spherical shaped particles and filamentous particles. In another embodiment of this composition in which the total amphiphilic diblock copolymer comprises between 82 to 95% by weight of the hydrophobic polymer block, the composition comprises primarily filamentous particles.

These compositions containing filamentous particle have particular utility in drug delivery. For instance, other non-spherical, oblong particles can be internalized by cells (Champion, J. A.; Mitragotri, S., *Proc Natl Acad Sci USA* 2006, 103, (13), 4930-4) and useful for controlled delivery (Son, S. J. et al, *J Control Release* 2006, 114, (2), 143-52). The unique filamentous morphology of compositions described herein offers several advantageous features. For instance, the relatively extensive length translates into a high potential volume for drug cargo loading while the small cross section retains the carrier's nano status. Other filamentous nanostructures have shown the potential for unprecedented extended circulation (likely due to alignment with flow), allowing a novel extended release depot delivery system (Cai, S. et al, *Pharm Res* 2007 24, 2099-2109; Geng et al, *Nat. Nano* 2007, 2(4):249-255; Geng, et al, *Polymer* 2006, 47(7), 2519-2525)).

Another composition described herein comprises polymeric nanocarrier-encapsulated protein particles comprising (a) a therapeutic protein having a molecular weight of up to or equal to 300,000 Da; and (b) an amphiphilic diblock copolymer having a molecular weight of about 10,000 to about 100,000 Da and comprising a conjugate of a hydrophilic polymer block and a hydrophobic polymer block, wherein the total amphiphilic diblock copolymer comprises about 60 to 80% by weight of the hydrophobic polymer block. This composition comprises spherical particles with diameters of about 250 to 350 nm.

These compositions are produced by a double emulsion formulation without inactivation of the encapsulated protein, wherein the size and shape of the protein composition and protection of the protein against external proteolysis and mechanism of degradation of the nanocarriers are controlled by the weight percentage of the hydrophobic polymer block in the total amphiphilic diblock copolymer. These compositions prolong enzymatic activity and protect enzymatic activity from premature deactivation. Either spherical or filamentous compositions can be permeable for the substrates of the encapsulated active enzymes, such as freely diffusible $H_2O_2$, the catalase substrate.

The components of the above described methods and compositions are described in detail below.

Amphiphilic Copolymer

In certain embodiments, an amphiphilic diblock copolymer comprising a hydrophobic block polymer and a hydrophilic block polymer, useful in these methods and compositions has a molecular weight of between about 10,000 to about 100,000 Da. In one embodiment, such an amphiphilic diblock copolymer has a molecular weight of about 10,000 to about 40,000 Da. In certain other embodiments, the amphiphilic diblock copolymer has a molecular weight of at least 10,000 Da, 20,000 Da, 30,000 Da, 40,000 Da, 50,000 Da, 60,000 Da, 70,000 Da, 80,000 Da, 90,000 Da, up to 100,000 Da. The amphiphilic diblock copolymer is also permeable to substrates of the encapsulated protein, which is discussed below. In other embodiments, the diblock copolymer may be replaced with an amphiphilic triblock or multiblock copolymer.

The hydrophobic and hydrophilic block copolymers useful in the methods and compositions herein are desirably composed of a polymeric-backbone having functional (e.g., pendant side chain or endcapped) groups for physically crosslinking with other entities, including affinity moieties, therapeutic entities, or other polymers. Functional groups encompass conjugatable groups such as amines, hydroxyls, carbonyls, thiols, and carboxylic acids for covalently bonding of other bioactive molecules to the surface of the polymeric nanocarrier. The linkages formed following conjugation of the bioactive molecules to the conjugatable groups include amides, esters, and thioethers, among others.

A suitable hydrophobic polymer block of the amphiphilic diblock copolymer includes, without limitation, a poly(lactic acid) polymer, a polymer having amphiphilicity similar to that of a poly(lactic acid) polymer, such as a polycaprolactone polymer, a polyglycolic acid and their associated copolymers, e.g., poly(lactide-co-glycolide) at all lactide to glycolide ratios, and both L-lactide or D,L-lactide. In particular embodiments, a polylactic acid (PLA) is employed.

A suitable hydrophilic polymer block includes, without limitation, polypyrrolidone, poly(amino acids), polyether, polysaccharide or polyacrylic acid and its hydrophilic ester derivatives; and hydrophobic blocks, e.g., polyanhydrides, polydioxanones, polyphosphazenes, polyesters, polylactones, polyfumarates, polymers of alpha-hydroxy carboxylic acids, polyhydroxybutyric acid, polyorthoesters, polycaprolactone, polyphosphates, or copolymers prepared from the monomers of these polymers. In one embodiment the hydrophilic polymer block of the amphiphilic diblock copolymer is a modified or unmodified polyethylene glycol. The modified polyethylene glycol is selected from the group consisting of methoxypolyethylene glycol, amine modified polyethylene glycol, biotinylated polyethylene glycol, and an alkyne terminated polyethylene glycol. Generally PEG polymers for use herein have a molecular weight of from about 1000 to about 7500 Da, or more suitably with molecular weights of from about 3000 to about 6000 Da. In certain embodiments, the hydrophilic domain of the block copolymer has a molecular weight in the range of 100 to 20000 Da. In one embodiment, the hydrophilic block of the copolymer exists as an ester end-capped form. In another embodiment, the hydrophilic block of the copolymer exists in its native form providing linkage sites for an affinity moiety.

The ratio of the hydrophobic block polymer molecular weight to the total diblock copolymer molecular weight may be calculated as described in the examples below. Number average molecular weights ($\overline{M_n}$) of bulk copolymers are determined using a conventional technique, such as proton nuclear magnetic resonance. The weight average molecular weights ($\overline{M_w}$) and polydispersity indices (PDI) are determined by gel permeation chromatography. The ratio of the hydrophobic block copolymer MW to the total diblock MW is defined as the wt % of the hydrophobic block copolymer. The polydispersity indices (PDI) of the polymers are defined by the formula $\overline{M_w}/\overline{M_n}$, and determined using GPC.

As noted above, for the amphiphilic diblock copolymers to operate in the methods defined herein and produce the desired nanocarrier particle morphology the above noted ratio, or weight percentage of the hydrophobic copolymer block is equal to or greater than about 81% to produce a filamentous shaped particle, or between 80-81% to produce a mixture of spherical and filamentous particles, and less than 80% to produce spherical particles.

In an embodiment provided by the examples below, the amphiphilic diblock copolymer of the methods and compositions has a polyethylene glycol (PEG) as its hydrophilic block and a polylactic acid polymer (PLA) as its hydrophilic block.

Protein for Encapsulation

In all of the above polymeric nanocarriers (PNCs) produced by these methods, the encapsulated protein or mixture of two or more proteins, is not inactivated.

A biologically active protein, as used in the context of the present invention, includes without limitation, structural proteins such as albumins, globulins, histones, collagens, elastins, and keratins; and proteins with a chemical function to fulfill, e.g., enzymes, protein molecules united with non-protein molecules to produce compound proteins such as nucleoproteins, mucoproteins, lipoproteins and metalloproteins. A protein useful in the methods and compositions herein is naturally-occurring, synthetic or semi-synthetic.

In one embodiment, the protein is suitable for therapeutic or diagnostic use. Functionally active proteins that are particularly useful for encapsulation in the instant polymeric nanocarrier include clinically relevant proteases and their inhibitors such as serpins, growth factors and hormones, enzymes, e.g., anticoagulants and fibrinolytic plasminogen activators, interferons and cytokines, antibodies, antibody fragments and their conjugates with toxins and other biologically active agents. Among useful enzymes for encapsulation in the PNCs described herein are an antioxidant enzyme which is capable of reducing oxidative damage by decomposing or degrading reactive oxygen species. Antioxidant enzymes particularly useful include, without limitation, catalase, glutathione peroxidase, superoxide dismutase, hemeoxygenase, glutathione-S-transferase, or synthetic or mimetic enzymes thereof.

In another embodiment, the encapsulated protein is an enzyme that detoxifies a xenobiotic such as insecticides, drugs, pharmaceutical agents, organic chemicals, chemical warfare agents, toxins (including endotoxins), and the like which can have an adverse effect on a subject. Xenobiotic detoxifying enzymes particularly suitable for encapsulation in the instant polymeric nanocarrier include, but are not limited to, cytochrome P450 enzymes such as Cyp3A4 and Cyp3A5, Cyp1A1, Cyp1A2, Cyp2D6, Cyp2E1, Cyp2C, Cyp2C9, Cyp2B6, Cyp2C19 and the like which are responsible for the metabolism of a variety of drugs including cyclosporin, nifedipine, warfarin, phenacetin, caffeine, aflatoxin B1, ethanol, carbon tetrachloride, coumarin, sparteine, cyclophosfamide. Suitable enzymes further include alcohol dehydrogenase; epoxide hydrolase; glucuronyl transferases (detoxifying phenols, thiols, amines, and carboxylic acids); sulfotransferase (detoxifying phenols, thiols, and amines); N- and O-methyl transferases (detoxifying phenols and amines); N-acetyl transferase (detoxifying amines); and other peroxisomal enzymes including peroxidases, catalase, phytanoyl-CoA hydroxylase, and α-methylacyl-CoA racemase. In cases where the xenobiotic is of an unknown origin, it is contemplated that a polymeric nanoparticle containing a plurality of detoxifying enzymes can be employed to facilitate detoxification of the unknown agent.

Still other enzymes that are suitable for encapsulation in the PNC described herein are useful in diagnostic applications and are referred to generically as reporter enzymes. Such suitable enzymes include, without limitation, horseradish peroxidase, xanthine oxidase, Protein C, Superoxide Dismutase, NADPH oxidase, P450 oxidases, β-glucouronidase, luciferase, β-galactosidase, as well as other known enzymes conventionally employed in diagnostic assays. Additional such enzymes may be identified in standard texts and in catalogs of pharmaceutical and diagnostic reagents.

Substrates of the Protein

Substrates of the encapsulated protein to which the amphiphilic block copolymer is permeable include, well-known substrates of the specific enzymes selected, i.e., those proteins on which the enzymes acts. The substrate for the encapsulated enzyme of a composition described herein is freely diffusible through the polymer material of the nanoparticles, which permits prolonged enzymatic activity by the polymeric nanocarrier-encapsulated protein particles protecting protein from proteolysis. For example, suitable substrates of the encapsulated protein to which the amphiphilic block copolymer is permeable include, without limitation, hydrogen peroxide, o-phenylenediamine, hypoxanthine, cytochrome P450 enzyme substrates including 7-benzyloxy-4-trifluoromethylcoumarin, 7-ethoxycoumarin, 7-methosy-5-trifluoromethylcoumaring, 7-benzyloxyquinoline, or 7-benzyloxy-4-trifluyoromethylcoumarin; epoxy hydrolase enzyme substrates such as 2S,3S)-trans-3-Phenyl-2-oxiranylmethyl 4-nitrophenyl carbonate; methyl transferase enzyme substrates such as N-Acetyl-S-geranylgeranyl-L-cysteine; peroxidase enzyme substrates such as N-(4-Aminobutyl)-N-ethylisoluminol, 3-(4-Hydroxyphenyl)propionic acid, 2,2'-Azino-bis(3-ethylbenzothiazoline-6-sulfonic acid) diammonium salt, 3-Amino-9-ethylcarbazole, 4-Aminophthalhydrazide monohydrate, 3-Amino-9-ethylcarbazole, 4-Aminoantipyrine, 5-Aminosalicylic acid, 2,2'-Azino-bis (3-ethylbenzothiazoline-6-sulfonic acid), 4-Chloro-1-naphthol, 4-Chloro-7-nitrobenzofurazan, 3,3'-Diaminobenzidine, o-Dianisidine dihydrochloride, Dicarboxidine dihydrochloride, Sodium 3,5-dichloro-2-hydroxybenzenesulfonate, Dihydrorhodamine, o-Dianisidine dihydrochloride, 3-(Dimethylamino)benzoic acid, Guaiacol, Iodonitrotetrazolium chloride, Neotetrazolium chloride, o-Phenylenediamine, o-Phenylenediamine dihydrochloride, Pyrogallol, 3,3'-Diaminobenzidine, Tetramethylbenzidine dihydrochloride, Tetramethylbenzidine, and hydrogen peroxide. Other enzyme substrates are hereby incorporated by reference from the reagents catalog available from Sigma Aldrich (St. Louis, Mo.).

Affinity Moiety

For use in both the methods and compositions described herein an affinity moiety may be used to modify the outer surface of the polymeric nanocarrier-encapsulated protein particle. An affinity moiety refers to any material or substance which can promote targeting of the PNC compositions described herein to particular cells, tissues and/or receptors in vivo or in vitro. The affinity moiety can be synthetic, semi-synthetic, or naturally-occurring. Exemplary affinity moieties include, without limitation, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs, oligonucleotide aptamers, and polynucleotides. Particularly suitable affinity moieties include molecules which specifically bind to receptors or antigens found on vascular cells. Other suitable affinity moieties target endothelial receptors, tissues or other targets accessible through a body fluid or receptors or other targets upregulated in a tissue or cell adjacent to or in a bodily fluid. For example, affinity moieties attached to nanocarriers designed to deliver proteins to the eye can be injected into the vitreous, choroid, or sclera; affinity moieties attached to nanocarriers designed to deliver proteins to the joint can be injected into the synovial fluid; or affinity moieties to the spine and brain can be delivered into the cerebral spinal fluid.

The affinity moiety can have other effects, including therapeutic effects, in addition to specifically binding to a target. For example, the affinity moiety can modulate the function of an enzyme target. By modulating cellular function, the affinity moiety is meant to alter/enhance cellular response when compared to not adding the affinity moiety. In most cases, a desired form of modulation of function is inhibition. Examples of affinity moieties which can have other functions or effects include agents such as Combrestastatin A4 Prodrug (CA4P) which can be used as a vascular affinity moiety that also acts as an anti-angiogenesis agent; and Cidecin, a cyclic lipopeptide, used as a bactericidal and anti-inflammatory agent.

Exemplary affinity moieties attached to the polymeric nanocarrier described herein include, but are not limited to, an antibody or fragment thereof which binds a selected cell surface receptor. An exemplary cell surface receptor is a cell adhesion molecule, such as, platelet-endothelial cell adhesion molecule (PECAM-1) or inter-cellular adhesion molecule (ICAM-1). Other affinity moieties include peptides such as RGD-containing peptides (see, e.g. U.S. Pat. No. 5,866,540); bombesin or gastrin-releasing peptide; and peptides designed de novo to be complementary to tumor-expressed receptors, antigenic determinants, or other receptor targeting groups. These affinity moieties can be used to control the biodistribution, non-specific adhesion, and blood pool half-life of the polymeric nanocarrier compositions.

In particular embodiments, the affinity moiety is attached by covalent means. In another embodiment, the attachment is by non-covalent means. For example, antibody affinity moieties can be attached by a biotin-avidin biotinylated antibody sandwich to allow a variety of commercially available biotinylated antibodies to be used on the coated polymeric nanocarrier. In other embodiments, the affinity moiety is added in a single step, e.g., through the coupling of biotinylated nanocarriers and antibody-streptavidin chemical conjugate or fusion construct.

Methods of Use

The compositions described herein may be adapted for use in diagnostic or therapeutic methods, depending upon the identity of the encapsulated protein. Polymeric nanocarrier compositions described herein can be administered to any animal, desirably to mammals, and more desirably to humans. The composition described above, or prepared as described above, are anticipated to be stable when administered in vivo to a human subject, based upon the in vitro stability data illustrated in FIGS. 5A-5D and 6A-6H.

In one embodiment, therefore, a PNC as described herein containing a therapeutically active protein is administered to a subject or tissue thereof in vivo or ex vivo for treatment of a disease responsive to the presence of that protein. In one embodiment, these compositions are useful when administered ex vivo for organ transplantation. Exemplary diseases or conditions requiring therapeutic intervention include, without limitation, oxidative stress, atherosclerosis, stroke, hypertension, inflammation, acute Lung Injury (ALI/ARDS), thrombosis, ischemia-reperfusion injury, organ transplantation, diabetes, angina and myocardial infarction.

An antioxidant enzyme encapsulated in the instant polymeric nanocarrier is particularly useful in methods for detoxifying reactive oxygen species including the superoxide anion radical ($O_2^-$), hydrogen peroxide ($H_2O_2$), hypochlorous acid (HOCl), hydroxyl radical (OH.), and singlet oxygen ($^1O_2$) which are generated in the body, mediating cell damage and apoptosis.

When the instant polymeric nanocarrier contains art antioxidant enzyme and an affinity moiety for targeting vascular endothelial cells, sustained therapy against vascular oxidative stress can be achieved for the prevention or treatment of pathological processes involved in disease conditions including atherosclerosis, hypertension, diabetes, stroke, myocardial infarction, acute lung injury, inflammation and ischemia-reperfusion injury. Administration of the nanocarrier-encapsulated antioxidant enzyme can be as in intervention in debilitating situations such as acute lung injury, sepsis (toxic shock), autoimmune diseases, etc., thereby limiting the progressive damage caused by ROS under these extreme oxidative stress situations.

When the instant polymeric nanocarrier contains an enzyme which detoxifies xenobiotics, the PNC can be used to reduce, inhibit, or ameliorate the effects of an intentional or unintentional exposure (including overdosing) to one or more xenobiotics. Moreover, compositions described herein can provide detoxifying enzymes to subjects with impaired liver function, e.g., due to alcoholism, fatty liver disease, biliary cirrhosis, and hepatocarinomas leading to lower detoxification activity in general, or suffering from a peroxisomal disorder such as hyperoxaluria, Refsum disease, and β-oxidation disorders.

In another embodiment, a PNC as described herein containing a reporter protein is administered in vitro to a cell culture or tissue culture for diagnostic or research purposes, as well as administered in vivo for diagnostic purposes. Such diagnostic methods may include detection of cancerous cells in tissue sections or explants or cell cultures or detection of any abnormal cell receptor when the PNC contains an affinity moiety capable of targeting that receptor or cell.

Administration of these compositions may include, without limitation, the following routes: intravenous, intranasal, topical, sublingal, ocular, buccal, parenteral, interperitoneal, intrathecal, subcutaneous, topical, oral, by aerosol, or local administration, into the vasculature, lungs, lymphatic system, synovial fluid, ocular fluid, or spinal fluid or other body tissues.

Differing administration vehicles, dosages, and routes of administration can be determined for optimal administration of the instant nanocarrier compositions; for example, injection near the site of an injury or tumor may be preferable for facilitating local treatment. For example, biodegradable nanocarriers encapsulating an anti-inflammatory (e.g., hydrocortisone) and growth factors (e.g., BDNF) can be administered via direct lumbar injection using a standard spinal tap procedure. Nanocarriers introduced into the cerebral spinal fluid are dispersed through this space via natural convective motion and accumulate at the wound site as a result of the enhanced permeation and retention (EPR) effect. Also, targeting can be further enhanced by the inclusion antibodies toward common inflammatory markers.

Generally, the nanocarrier compositions used in the invention are administered to an animal in an effective amount, which is defined as an amount of encapsulated protein effective to either reduce the symptoms of the disease sought to be treated or induce a pharmacological change relevant to treating the disease sought to be treated. Therapeutically effective amounts of the encapsulated proteins can be any amount or doses sufficient to bring about the desired effect and depend, in part, on the condition, type and location of the pathology, the size and condition of the patient, as well as other factors readily known to those skilled in the art. The dosages can be given as a single dose, or as several doses, for example, divided over the course of several weeks.

Depending upon the mode of administration and the condition being treated or diagnosed, a polymeric nanocarrier composition of the instant invention can be formulated with an excipient. See, e.g., Remington: The Science and Practice of Pharmacy, Alfonso R. Gennaro, editor, 20th ed. Lippincott Williams & Wilkins: Philadelphia, Pa., 2000.

As described in the examples below, the inventors prepared PNC composed of a series of diblocks combining a 5,000 MW hydrophilic polymer (e.g., PEG) block with hydrophilic polymer (e.g., PLA) blocks of diverse molecular sizes. Of note, these PNC are not typical self-assembled particles formed from solvent-free amphiphiles that have been re-hydrated with water. Rather, a more complex structure occurs with the present PNC that result from the freeze thaw double emulsion formulation (See FIG. 1A, blown up PNC cross section).

Based on PNC yield and enzyme loading data, copolymers containing 63-84% PLA have sufficient amphiphilicity for formulation of PNC with effective diameters on the order of 500 nm or less, and significant catalase activity that is markedly protected against external proteolysis. PNC in the sub-500 nm range are readily internalized when targeted to appropriate cell surface receptors and thus are useful candidates for intracellular delivery. Lower PLA content provided no significant PNC yield. The encapsulated enzyme, catalase, inactivation was more profound in more hydrophobic polymers (93% and 100% PLA). The enhanced hydrophobicity of these PNC translates into stronger protein-surface interactions and adsorption that may interfere with the enzyme's activity (Shuvaev, V. V. et al, *J Control Release* 2007, 118, (2), 235-44).

Double emulsion formulations typically produce PNC with both encapsulated and surface adsorbed protein loads. Polymer amphiphilicity appears to control this ratio. Surface adsorbed protein is not protected against proteolysis, as appears to be the case for less amphiphilic, and thus more hydrophobic, 93% PLA PNC. However, filamentous 84% PLA PNC provided protection of encapsulated catalase comparable to that of spherical 78% PLA PNC. This notion of surface adsorption versus encapsulation coincides with the observed enzyme protection from proteolysis for the spherical PNC observed in the 80% PLA range, as has been proven with this system for a similar PEG PNC that was ~80% PL(G)A. It is unlikely that degradation of the polymer itself would contribute to enzyme inactivation. There is no detectable change in either polymer MW by GPC (data not shown) or PNC number over the course of 1 day, the timeframe within which catalase activity studies were performed. Further, cross sectional diameters of 93% PLA filamentous PNC are much smaller than those observed for 84% PLA filamentous PNC (35.4±5.3 nm vs. 68.3±7.3 nm, respectively).

From a geometric standpoint, the 93% PLA filamentous PNC possessed only 26% of the internal volume per unit length afforded to the 84% filamentous PNC, suggesting that the degree of encapsulation may be dependent upon filament diameter. In other words, the ratio of encapsulated to surface-adsorbed catalase is expected to be lower in 93%, relative to 84%, PLA filamentous PNC, explaining the loss of protease resistance observed in the former formulation.

The PLA MW also controlled shape and degradation of the formed PNC. In the case of spherical PNC, a decrease in PNC number with stable mean diameter is characteristic of bulk erosion and homogeneous degradation of particles: the nominal diameter remains stable until the PNC erodes throughout to a burst point, diminishing the net number of PNC. This coincides with degradation properties observed with polyester PLA and PLGA nano-structures (von Burkersroda, F. et al, *Biomaterials* 2002, 23, (21), 4221-31; Gopferich, A., *Macromolecules* 1997, 30, (9), 2598-2604). Lowering the pH and polymer MW accelerates the PNC degradation, most likely due to accelerated polymer hydrolysis.

Conversely, the gradual decrease in effective diameter and corresponding increase in number of particles (FIG. 5C, 5D), unexpected for homogeneously degrading nanoscale polyester structures, are suggestive of an alternative mechanism of degradation of filamentous PNC. Filamentous PNC fragment into shorter filaments and eventually spheres. Thus, this form of degradation serves as a depot of spherical, more diffusible carriers. Similar to spherical PNC, lowering the pH and polymer MW accelerated degradation of the filamentous PNC (FIGS. A-8H). This raises an interesting point regarding DLS analysis of non-spherical particles. Light scattering is proportional to both the particle area and the number of particles. As the filamentous structures fragment and become spherical, the diffusion rate increases (resulting in a smaller hydrodynamic radius), but the average cross-sectional area of the light path increases, leading to an increase in scattering. Therefore, the obtained data reflect an increase in the number of particles. Disruption of filamentous PNC by ultrasound led to increased scattering intensity that reflected an increased number of PNC fragments.

These examples for the first time demonstrated simultaneous encapsulation and protection of an active enzyme within filamentous PNC. All chemicals and reagents used in the examples below were purchased from Sigma-Aldrich (St Louis, Mo.) and used as received unless otherwise stated.

As illustrated in the examples below, various PLA molecular weights (MW's), and consequently block copolymer MW ratios, were investigated in terms of resultant PNC morphology, enzyme loading and cargo protection from proteolytic degradation.

Example 1

Synthesis of Diblock Copolymers

DL-lactide was re-crystallized twice in anhydrous ether, before mixing with methoxy poly(ethylene glycol) (mPEG) MW 5,000 (Polysciences, Warrington, Pa.) in stoichiometric ratios to achieve desired molecular weights. Reactants were heated to 140° C. under nitrogen while stirring for 2 hours to remove trace water from samples. The temperature was reduced to 120° C. and stannous octoate (1 wt %) was added to catalyze the ring opening polymerization (ROP) of lactide with mPEG as the initiator. The polymerization was allowed to continue for 6 hours. The diblock copolymer was then dissolved in dichloromethane (DCM) and twice precipitated in cold diethyl ether. Residual solvent was then removed by first drying via rotary evaporation (SAFETY VAP® 205 system, Buchi, Switzerland), followed by lyophilization (RCT 60, Jouan, Winchester, Va.).

Number average molecular weights ($\overline{M_n}$) of bulk copolymers were determined using proton nuclear magnetic resonance ($^1$H-NMR). The weight average molecular weights ( $\overline{M_w}$) and polydispersity indices (PDI) were also determined by gel permeation chromatography (HPLC-GPC), with a Binary HPLC pump (1525, Waters, Milford, Mass.), a Refractive Index Detector (2414, Waters) and three serial 7.8×300 mm STYRAGEL® columns (Waters) using tetrahydrofuran (THF) as the mobile phase. Chromatograms were analyzed using Breeze version 3.3 software with polystyrene standards used for calibration.

Table 1 reports data for synthesized polymer characterization. Number and weight average molecular weights are indicated by the symbols ($\overline{M_n}$ and $\overline{M_w}$, respectively). The resultant wt % PLA, or "% PLA", defined as the ratio of PLA MW to the total diblock MW, is also shown in Table 1. The polydispersity indices (PDI) of the polymers are defined by the formula $\overline{M_w}/\overline{M_n}$, and determined using GPC. Actual % PLA, or wt % PLA, is defined as the ratio of the actual PLA block $\overline{M_n}$ to the entire diblock copolymer $\overline{M_n}$.

By controlling reaction feed ratios, ring-opening polymerization (ROP) of lactide with a monomethoxy-capped mPEG initiator yielded mPEG-PLA with PLA block MW's from 800 Da to 64,000 Da as determined by $^1$H-NMR. All diblocks contain a methoxy end-capped 5,000 MW mPEG, which served as the initiator for the ring opening polymerization (ROP) of lactide into PLA. As noted in the Table 1, PDI slightly increased with increasing MW, from 1.1 for smaller PLA polymers to 1.8 for the largest ones, as expected for ROP products.

TABLE 1

Enzyme in Filamentous and Spherical Polymer Nanocarriers
Synthesized Polymer Characterization[a]

| Target PLA $M_n$ | PLA $M_n$[b] | % PLA | PLA $M_n$[c] | PLA $M_w$[c] | PDI |
|---|---|---|---|---|---|
| 1000.0 | 791.0 | 13.7 | 6032.8 | 6629.4 | 1.1 |
| 5000.0 | 2956.2 | 37.2 | 5666.2 | 6190.2 | 1.1 |
| 8000.0 | 6575.5 | 56.8 | 3898.9 | 7253.0 | 1.4 |
| 10000.0 | 8482.7 | 62.9 | 9974.1 | 11649.9 | 1.1 |
| 20000.0 | 18226.7 | 78.5 | 23236.7 | 36908.2 | 1.5 |
| 25000.0 | 21252.7 | 81.0 | 21497.8 | 34530.8 | 1.5 |
| 30000.0 | 27091.3 | 84.4 | 21859.0 | 35792.4 | 1.5 |
| 35000.0 | 34557.6 | 87.4 | 21079.4 | 39442.7 | 1.7 |
| 65000.0 | 64330.2 | 92.8 | 19169.4 | 37650.1 | 1.8 |

[a]indicates that the measurement was determined by $^1$H-NMR

[b]indicates that the measurement was determined by GPC.

The formulation scheme utilized throughout these studies for nanocarrier synthesis and protein encapsulation, and the resultant morphology is illustrated in FIG. 1A.

Example 2

Nanoparticle Formation

A freeze-thaw double emulsion solvent evaporation technique was used as previously described in Dziubla et al 2005 cited above and US Patent Application Publication No. 2006/0127386. Briefly, mPEG-PLA diblock copolymer is dissolved in DCM at 25 mg/ml. A 1 mg/ml bovine liver catalase (242 kDa) (Calbiochem, EMD Biosciences, San Diego, Calif.) solution and a polyvinyl alcohol (PVA) surfactant solution (2 wt %, 87-89% hydrolyzed, $M_w$=13,000-23,000) in 20 mM PBS are prepared. The primary emulsion consisted of the organic phase (1 ml polymer-DCM mixture) and the aqueous phase (100 μl catalase solution) homogenized at 15 krpm for 1 minute in a dry ice-acetone bath with a 7 mm-blade homogenizer (KINEMETICA POLYTRON 3100 instrument with a PDTA3007/2 generator, Brinkmann Instruments, Westbury, N.Y.). The primary emulsion was then added to 5 ml of the PVA surfactant solution and homogenized at 15 krpm for 1 minute. The resultant mixture was added to 10 ml of PVA solution and stirred overnight to allow removal of the residual solvent. The microparticle fraction was removed by a primary centrifugation at 1,000 g for 10 minutes. The nanoparticle fraction was collected by subsequent centrifugation at 20,000 g for 30 minutes. The supernatant was then removed and the PNC pellet was re-suspended in PBS and purified again by further centrifugation.

Example 3

Enzyme Loading Determination

Protein loading was determined via radioisotope labeling and enzymatic activity. Loading via radiolabeling was determined as described before, by formulating PNC with $^{125}$I-labeled catalase following the directions of the above-referenced in Dziubla et al 2005 cited above. Catalase was radiolabeled with Na$^{125}$I (Perkin Elmer, Boston, Mass.) via the Iodogen method (Pierce Biotech., Rockford, Ill.). Unbound $^{125}$I was removed from catalase using BIOSPIN 6 columns in accordance with the manufacturer's instructions (Bio-Rad labs, Hercules, Calif.). Total solution $^{125}$I-catalase content was measured before centrifugation, and then radioactivity of the $^{125}$I-catalase/PNC-composed pellet after centrifugation was measured. A WIZARD 1470 gamma counter (Wallac, Oy, Turku, Finland) was used for radiotracing.

To determine loading via enzymatic activity, a catalase activity assay (Shuvaev, V. V. et al, *Methods Mol Biol* 2004, 283, 3-1) was used, both for the total sample before and after centrifugation. Briefly, 900 μl of 5 mM $H_2O_2$ in PBS and 100 μl of enzyme-loaded PNC was added to a quartz cuvette. The kinetics of $H_2O_2$ degradation was then measured with a spectrophotometer at 242 nm (absorbance at this wavelength corresponds to the $H_2O_2$ concentration; 1 Unit=23, ΔAbs/ml).

Example 4

Catalase Protection Against Proteolysis

Protection against proteolysis was tested as described previously in Dziubla et al 2005 cited above. Briefly, PNC preps loaded with $^{125}$I-catalase were incubated with a 0.2 wt % protease (pronase) solution at 37° C. in a shaker bath set at 60 rpm for 1 hour. Samples were removed and centrifuged at 16,000 g for 20 minutes. Supernatant containing degraded protein and pellet containing intact protein encapsulated within PNC were collected and counted.

Example 5

In Vitro Degradation of PNC

Solutions of neutral physiologic (pH 7.4) PBS, moderately acidic lysosomal-mimetic (pH 5.0) MES, and strongly acidic (pH 2.5) sodium citrate were prepared. A buffer concentration of 150 mM was selected for these solutions to ensure that the buffering capacity would not be saturated during polymer degradation and lactic acid accumulation. Based upon the Henderson-Hasselbach equation, complete degradation of $PNC_{65kDa}$ polymer would result in a maximum pH change of 0.011. PNC formulations were incubated in these buffer solutions in a shaker bath at 37° C., shaking at 60 rpm to minimize sedimentation (50-Reciprocating Shaker Bath, Precision-Jouan, Inc., Winchester, Va.). Samples for transmission electron microscopy (TEM), GPC and lactic acid content assays were taken weekly over the 28-day duration of the study.

Example 6

PNC Size Determination

Aliquots of 20 μl (for PNC size measurements) collected at the onset of the study and every 3 days afterwards were placed in NMR tubes and diluted with 200 μl of the appropriate pH buffer in triplicate. Size and relative number of PNC, proportional to measured scattering intensity, were determined via dynamic light scattering (DLS, 90PLUS Particle Sizer, Brookhaven Instruments, Holtsville, N.Y.). When a classical scattering expression for PNC is adapted, it is evident that the average intensity of the scattered light is proportional to the actual number of scattering components present in the sample, i.e. $(I) \propto N\, M^2 P(\theta)$, where N is the number of independent particles of size, M, and P(θ) is the sample scattering factor at scattering angle θ (Brown, J. C. et al, *Journal of Chemical Physics* 1975, 62, (3), 1136-44; Tanford, C., *Physical Chemistry of Macromolecules*. Wiley: New York, 1961; p 710). While there exist novel methods for counting the precise number of nanoparticles (Epstein, H. et al, *Biomaterials* 2006, 27, (4), 651-9), the relative number as determined by scattering intensity is adequate for this study.

Example 7

PNC Concentration Determination

PNC yield was determined via a calorimetric PEG assay based on the PEG-Barium Iodide complex. Prior to the assay, two solutions were prepared: solution A, consisting of 2.4 g of Barium chloride, 8.0 ml of 6 M HCl and 32 ml of deionized (DI) water, and solution B, consisting of 800 mg of potassium iodide, 500 mg of iodine, and 40 ml of deionized (DI) water. A 50 μl aliquot of PNC sample was hydrolyzed by adding 200 μl of 5 M NaOH and incubating overnight at 80° C. The pH of hydrolyzed PNC samples was then neutralized by addition of 5 M HCl and 20 μl aliquots were added to a multiwell plate and diluted to a 170 μl total volume with DI water. Subsequently, 40 μl of undiluted solution A and 1:5 diluted solution B were then added to each well. After a 10 minute incubation at room temperature, absorbance of the colored product was measured at 550 nm using the microplate reader (Sims, G. E.; Snape, T. J., *Anal Biochem* 1980, 107, (1), 60-3). Standard solutions of PEG (5,000 MW) were used for calibration.

For 100% PLA PNC, an enzymatic assay based on the detection of lactic acid monomer was used. Samples were hydrolyzed to their monomer state and neutralized as described above. Aliquots were similarly added to a multiwell plate. Then 50 μl of the assay buffer, consisting of 100 μl of 50 mU of lactate oxidase, 100 μl of 10 U $ml^{-1}$ of horseradish peroxidase (HRP; Calbiochem, EMD Biosciences, San Diego, Calif.), and 50 μl of 10 mM 10-Acetyl-3,7-dihydroxyphenoxazine (AMPLEK RED dye; Molecular Probes, Eugene, Oreg.) in dimethyl sulfoxide (DMSO), were added to each well. Lactate oxidase produces hydrogen peroxide in the presence of lactic acid, and the formed $H_2O_2$ is decomposed by HRP in the presence of AMPLEX RED dye, forming the fluorescent RESORUFIN product. After incubating for 10 min at ambient conditions the RESORUFIN concentration was determined by UV absorbance at 550 nm on a microplate reader (Model 2550-UV, Bio-Rad Labs, Hercules, Calif.). Pure lactic acid solutions were used for calibration.

Example 8

PNC Morphology Study

PNC morphology was determined by fluorescence microscopy and transmission electron microscopy (TEM). For fluorescence microscopy, aliquots of PNC were stained with the lipophilic carbocyanine dye, PKH26, via established methods (Dalhaimer, P. et al, *Macromolecules* 2003, 36, (18), 6873-6877) and then imaged with a Nikon confocal microscope equipped with a 60× oil immersion objective. For electron microscopy, 5 μl of each sample were applied to a separate TEM mesh grid (FORMVAR FILM 200 Mesh, Electron Microscopy Sciences, Hatfield, Pa.) and excess was removed before drying. Samples were stained with filtered (0.1 μm filter) 2 wt % uranyl acetate (UA; Electron Microscopy Sciences, Fort Washington, Pa.) for 5 minutes in the dark and then washed with filtered DI water. Grids were dried at ambient conditions for 1 hour before they were imaged on a JEOL JEM-100CX TEM.

Example 9

PLA Content in PLA-PEG Diblock Controls PNC Yield and Morphology

PLA MW influenced yield and morphology of PNC formulated by the freeze thaw emulsification process (FIGS. 1B, 1C and FIG. 2). Final PNC concentration in the nano-scale fraction of the particles was determined by quantitative analysis of PEG or lactic acid content. For the 100% PLA PNC, polymer mass was determined solely by measuring lactic acid content. For the diblock copolymers, either assay could be used to measure total polymer mass in the PNC, due to the equimolar ratio of the PEG block to the PLA block. For example, using a PEG assay, the total mass of a diblock made with 5,000 Da PEG would be $$Diblock\ MW = \left\{\frac{x\ (\text{g}, PEG)}{5000\ (\text{g/mol}, PEG)} \times [y\ (\text{g/mol}, PLA)]\right\} + [x\ (\text{g}, PEG)].$$

The inventors found that diblocks containing 60 to 100% PLA provided a significant yield (FIG. 1B) of nano-scale particles with mean diameters ranging from 200 to 600 nm (FIG. 1C). A peak in yield and in effective diameter was also seen at ~80-90% PLA.

PLA MW determined PNC geometry in the range of 63-93% PLA content. An increase in hydrophobic PLA fraction above 80% resulted in an abrupt shift from spherical geometry to filamentous structures, evident from fluorescence microscopy (FIG. 1C, inset) and TEM (FIG. 2). The asymmetric morphology of PNC formed at >80% PLA complicates simple interpretation of DLS measurements (FIG. 1C) since the usual Stokes-Einstein equation assumes a spherical hydrodynamic radius. Therefore, size of filamentous PNC was estimated by microscopy. Fluorescence microscopy revealed that PNC with filamentous morphology are flexible in solution, similar to other PEG-diblock based filamentous micelles (Dalhaimer et al 2003, cited above; Dalhaimer, P. et al, *Journal of Polymer Science Part B—Polymer Physics* 2004, 42, (1), 168-176); and TEM of dried PNC shows the assemblies are not only filamentous, but also sufficiently robust to withstand drying.

Example 10

PLA Content in PLA-PEG Co-Polymer Modulates PNC Loading and Activity of Loaded Enzymes In order to circulate in the bloodstream without mechanical retention in capillaries, spherical-PNC should be submicron in diameter. The homogenization in the double emulsion formulation produces PNC of desired size (200-500 nm), yet also reduces enzyme activity and decreases loading of the enzyme drug. The freeze-thaw cycle aids synthesis of enzyme-loaded PNC by both enhancing the amount of loaded enzyme and protecting it from inactivation (Dziubla et al 2005, cited above). Here the inventors tested how loading and resultant activity of the catalase depend on the content of hydrophobic PLA in the PLA-PEG copolymer.

The inventors monitored PNC loading, defined here as the percent of catalase added in the primary emulsion that is entrapped in the nano fraction of formulated particles, via radioisotope tracing of $^{125}$I-labeled catalase. The enzyme mass loaded in the microsphere population was excluded from this study, as this regime is not useful for the intended drug delivery application of this technology platform. Catalase loading showed a minor peak at 80% PLA and a major peak at 93% PLA. The lowest loading occurred at the extremes of 0 and 100% PLA, respectively.

Figures 3A, 3B, 3C:
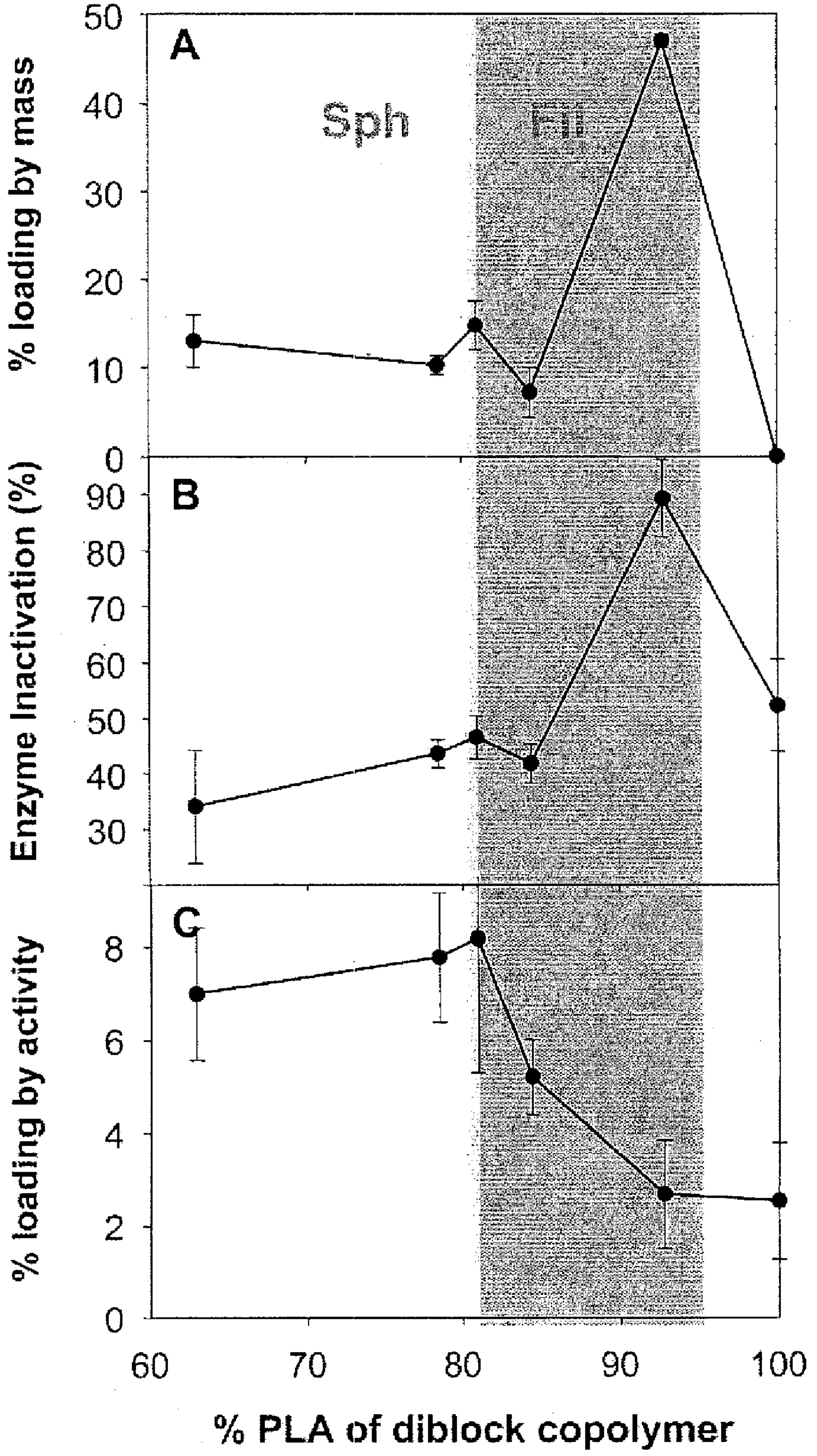
FIGS. 3A-3C show that amphiphilicity of exemplary diblock PEG-PLA copolymer controls PNC loading of an illustrative enzyme, i.e., catalase.

The highest catalase loading, 46.9%, was observed with 93% PLA (FIG. 3A). This result may represent both encapsulation and surface adsorption due to the enhanced hydrophobic nature of the dominant PLA block. Loading in the sub-60% PLA polymers was negligible (FIG. 3A), since PNC did not readily form in this range (FIG. 1B). When the PLA content was between 60-79% PLA, ≦500 nm spherical PNC were formed with an enzyme loading of 10%, similar to that reported in our previous study on loading catalase into PEG-PL(G)A PNC (Dziubla et al 2005, cited above). When the PLA content was increased over 81%, homogeneous filamentous PNC were formed (FIG. 2) with an enzyme loading of 7.2% (for 84% PLA), a loading value similar to that of the spherical PNC.

Important for function, the level of enzyme inactivation during encapsulation also varied as a function of PLA content. Activity loss was the lowest (34.1±10.2% to 41.8±3.6%) between 63% and 84% PLA (FIG. 3B). Compositions with PLA MW from 20 to 50% PLA, where there was a negligible PNC yield, caused profound enzyme inactivation (up to or equal to 90.9±1.2% activity loss, data not shown), possibly due to the enhanced surfactant nature of the polymers that could affect the protein tertiary structure. Similarly, 89.1±6.8% inactivation was observed when the highly hydrophobic 93% PLA polymer was utilized.

Therefore, PLA MW in the diblock regulated catalase loading (FIG. 3A) and resultant activity of the loaded enzyme (FIG. 3B). In order to normalize activity per loading the inventors defined percent of loaded activity as:

$$\%\ \text{Loading} = \left(\frac{\text{activity recovered in } PNC}{\text{added activity}}\right) \times (\%\ \text{activity recovered})$$

where % activity recovered factors in activity lost in the homogenization/formulation process. To the best of our knowledge, this method of loaded-catalase quantification has not been reported before, and it provides a more therapeutically relevant measure of enzyme loading, compared to protein mass loaded. The analysis shows that the percent of loaded activity was relatively high (approximately 5.2±0.8-8.2±2.9%) in the optimal range of 63-84% PLA polymers (FIG. 3C).

Example 11

Protection of Loaded Enzyme Against External Proteolysis

Figure 4A:
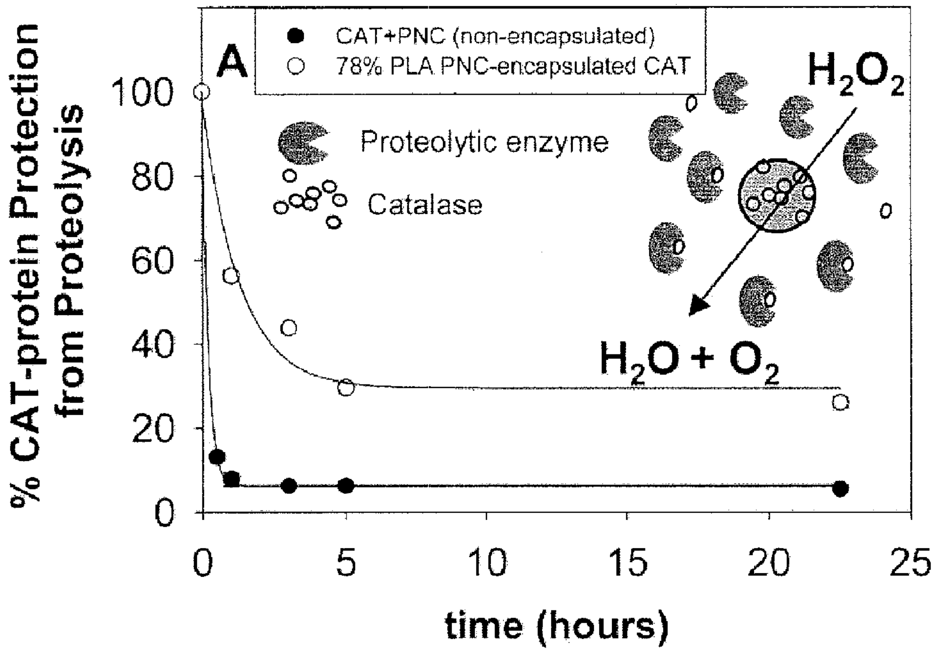
FIGS. 4A-4B are graphs showing that PNC protect catalase (CAT) from proteolytic degradation by a wide spectrum protease, pronase.

In the next series of experiments the inventors tested whether PLA content controlled the extent of protection of PNC-catalase against external proteolysis. First, the inventors determined the kinetics of proteolytic inactivation of catalase loaded into 78% PLA PNC (FIG. 4A). Free catalase was completely inactivated after incubation for one hour with the wide-spectrum protease, pronase, and thus this time is sufficient to test protection of PNC-encapsulated catalase against proteolysis. In this assay, formulations with a low PLA fraction (<60%) provided no measurable protection of catalase (not shown), presumably due to a lack of PNC formation (see FIG. 1B). The marginal protection observed at 100% PLA PNC is indicative of primarily surface adsorbed catalase, with no appreciable encapsulation to provide a physical barrier between catalase and a protease. This observation agrees with the proposed mechanism of encapsulation outlined in FIG. 1A that requires a well defined amphiphile, which 100% PLA is not.

Figure 4B:
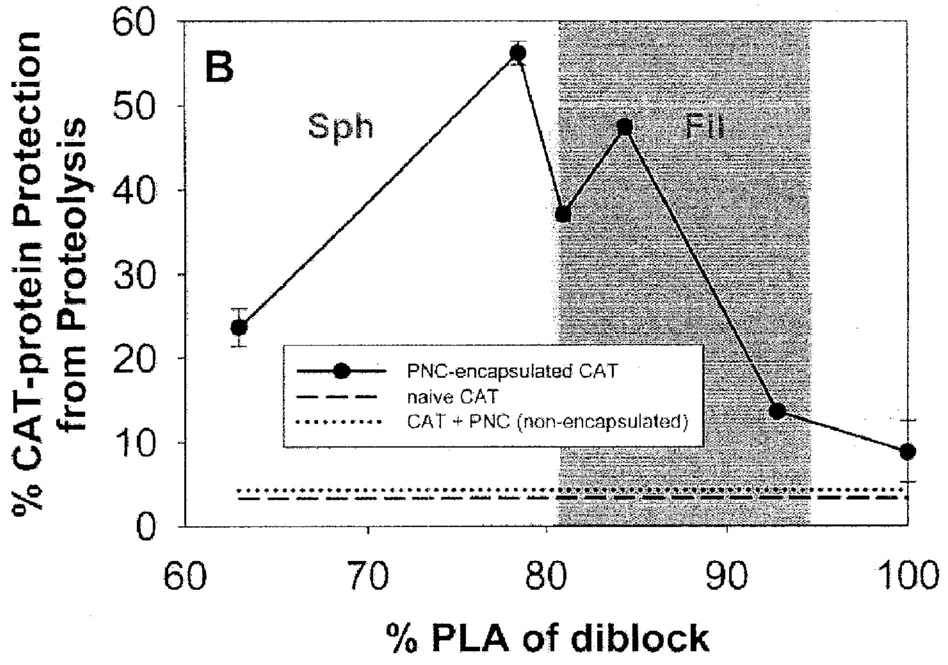

Loading of catalase into PNC produced with 63 to 84% PLA copolymer afforded significant protection against proteolysis (FIG. 4B). Loading catalase into PNC produced with 93% PLA copolymer provided little protection (13.6±0.3%), consistent with the hypothesis that the major fraction of the enzyme is surface-adsorbed in this rather hydrophobic filamentous PNC species. However, loading of catalase into either spherical or filamentous PNC, formed at 78% and 84% PLA, respectively, correspondingly provided 56.2±1.4% and 47.5±0.7% protection against proteolysis. Adding unloaded PNC to free catalase provided no protection against proteolysis (FIG. 4B, dashed lines), indicating that catalase adsorption on the PNC surface does not provide a secondary protective effect.

Example 12

PLA Content, pH of the Medium and PNC Geometry Modulate PNC Degradation

Figures 5A, 5B, 5C, 5D:
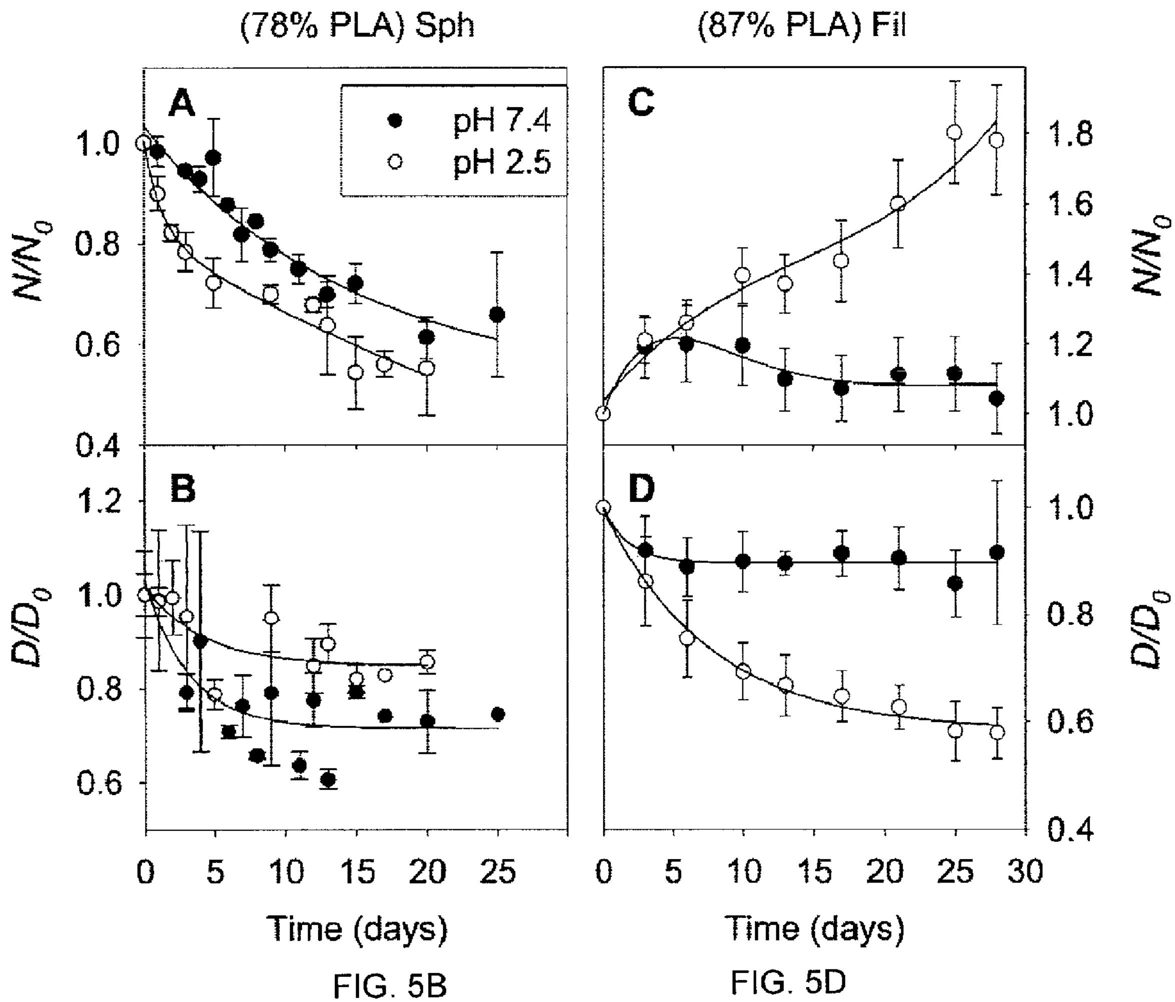
FIG. 5A shows the degradation of spherical (78% PLA) PNC by DLS as plotted against total number of PNC.
FIG. 5B shows the degradation of spherical (78% PLA) PNC by DLS as plotted against effective diameter. A bulk erosion phenomenon is evident from a decrease in the total number of PNC of FIG. 5A accompanied by a relatively constant measure in effective diameter.
FIG. 5C shows the degradation of filamentous PNC (87% PLA) by DLS as plotted against total number of PNC.
FIG. 5D shows the degradation of filamentous PNC (87% PLA) by DLS as plotted against diameter of PNC. Change in diameter of filamentous PNC is heightened at pH 2.5, while little change is seen at either neutral pH or pH 5.0 (data not shown). Effective diameters correlate with hydrodynamic volume occupied by filamentous PNC, which are coiled in solution as verified by fluorescence microscopy. Concomitant with a decrease in diameter was an increase in number of filamentous PNC in FIG. 5C. Similar trends were observed with higher MW (93% PLA) filamentous PNC.
Figures 6A, 6B, 6C, 6D, 6E, 6F, 6G, 6H:
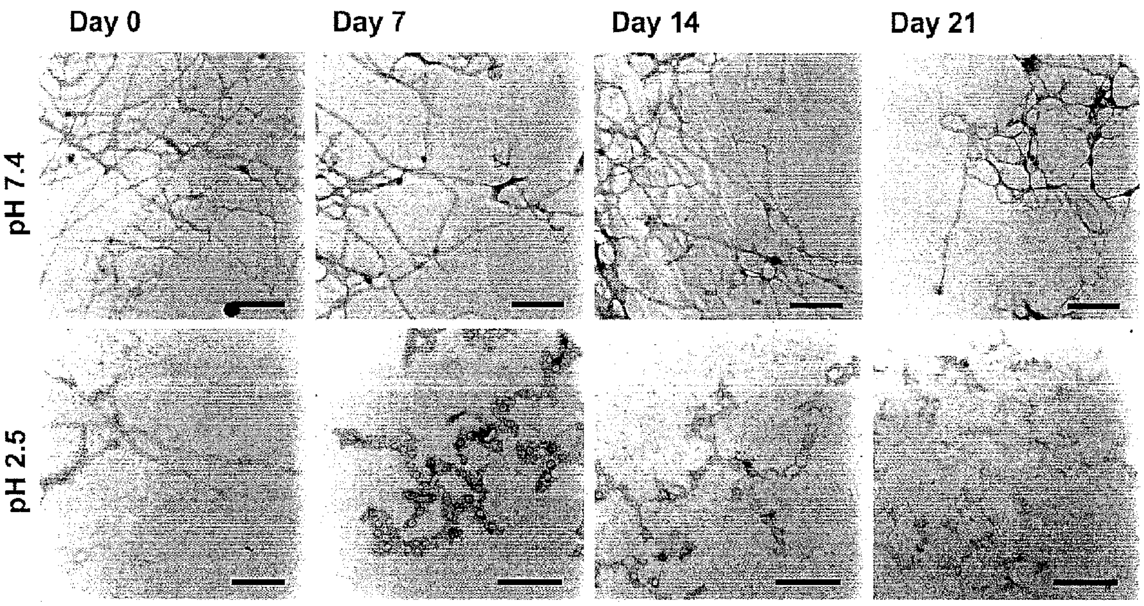
FIGS. 6A-6H are photomicrographs showing pH influenced degradation of filamentous PNC.
Figure 7:
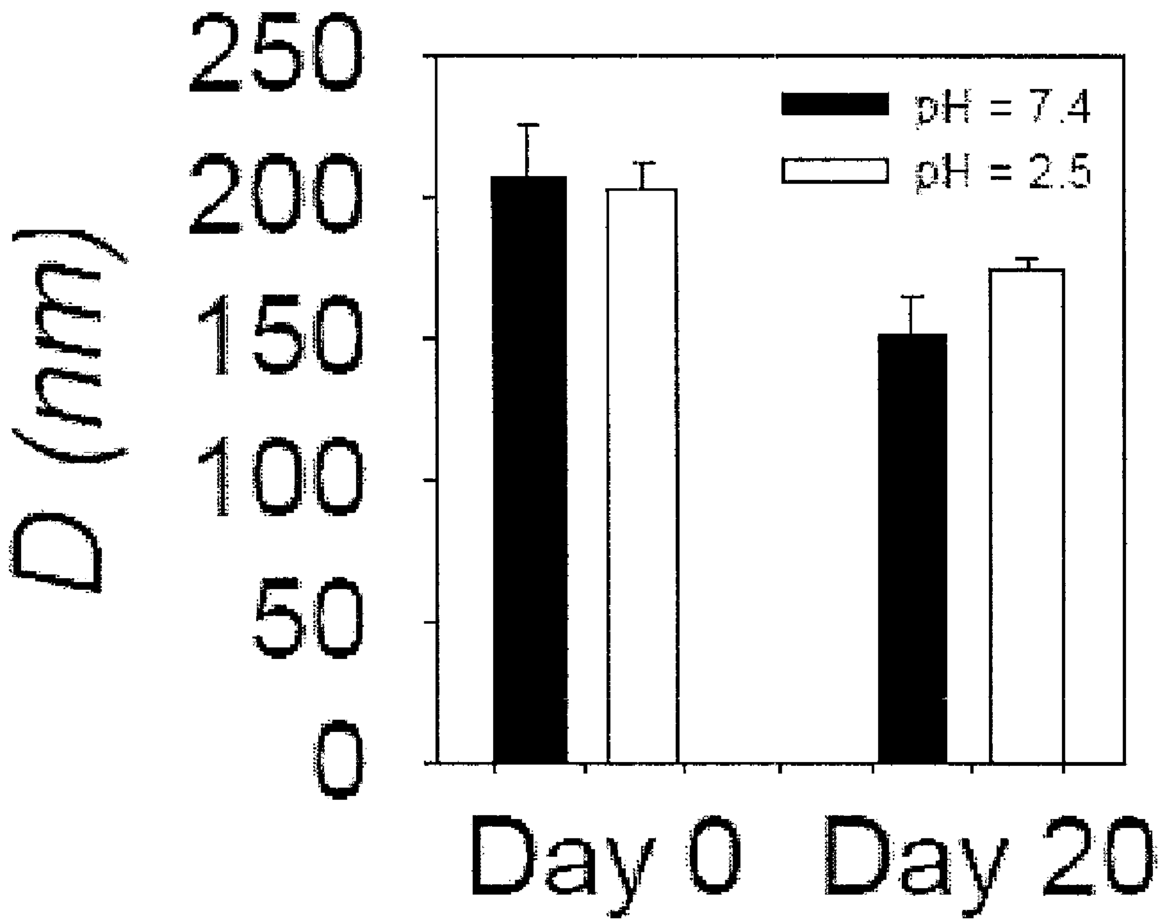
FIG. 7 is a bar graph showing effective diameters of degrading spherical PNC prepared by the methods disclosed herein exposed to two different pH conditions at Day 0 and Day 20. Initial and final sizes of degrading PNC are shown. There is very little change between initial and final time points, in terms of absolute diameter, even at very acidic pH.
Figures 8A, 8B, 8C, 8D, 8E, 8F, 8G, 8H:
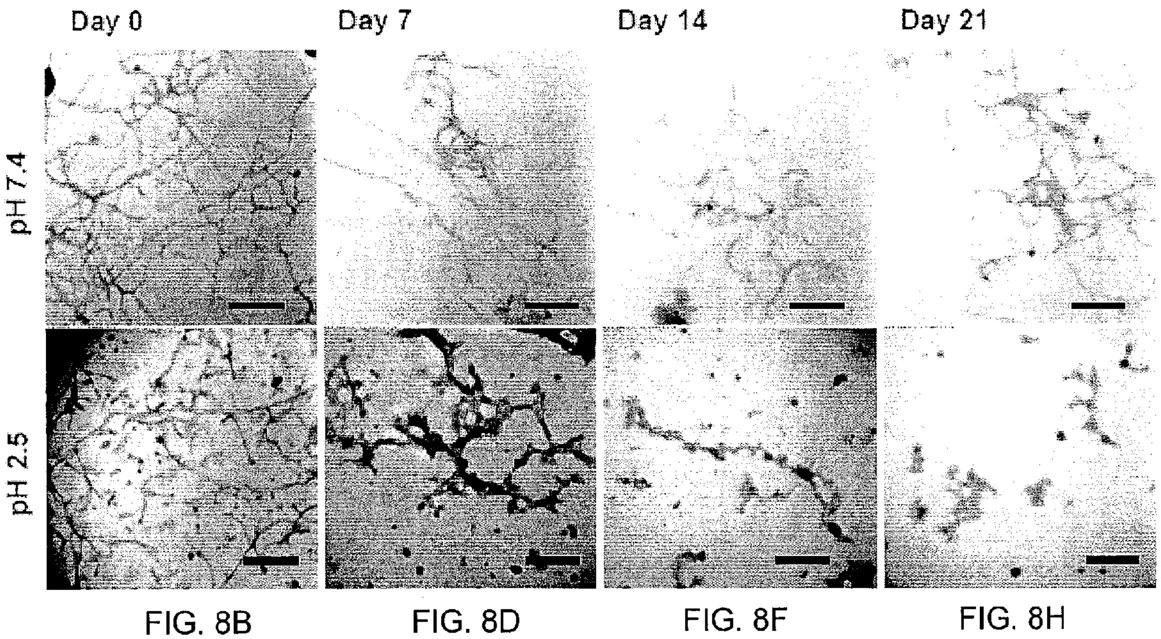
FIGS. 8A-8H are photomicrographs showing degradation of high MW (93% PLA) filamentous PNC over 21 days at two pH conditions.

To characterize copolymer PLA content control of PNC stability at physiologically relevant pH levels, degradation studies were performed at pH 7.4, 5.0, and 2.5, corresponding to normal blood plasma, lysosomal and stomach pH, respectively. DLS analysis of spherical PNC stability revealed a detectable decrease in the scattering intensity that can be directly correlated with the number of PNC in solution (FIG. 5A). There was only a marginal change in diameter of these spherical PNC over time, regardless of pH (FIG. 5B). This result likely reflects pH-modulated PNC degradation via bulk erosion rather than surface erosion. Thus, PNC with lower PLA MW (~80% PLA) decreased in number more rapidly with decreasing pH; the number of 80% PLA PNC dropped by ~35% at neutral pH, while at pH 2.5, the number of PNC decreased ~45% with a faster initial drop within the first week. Degradation at pH 5.0 was not significantly different than that at neutral pH (data not shown). Supplement FIG. 1 shows initial and final effective PNC diameters.

DLS analysis of filamentous PNC is complicated by their geometry and dynamic conformations in solutions. Thus, the effective size of filamentous PNC represents a complex function of their length, flexibility and coiling. Nevertheless, DLS measurements showed little change in either effective size or concentration of filamentous PNC formed at high PLA content (87% PLA) when incubated at neutral pH over a month (FIG. 5C, D, black circles). Importantly, electron microscopy confirmed this result (FIG. 6, row 1). In contrast, DLS analysis revealed a notable decrease in effective size of filamentous PNC at acidic pH, which correlated with an increase in the scattering intensity. This increased scattering implies an increased concentration of particulate matter, likely reflecting fragmentation of filamentous PNC (FIG. 5C, D, white circles). Again, this DLS result has been confirmed by electron microscopy that showed a gradual fractionation of filamentous PNC into shorter and eventually spherical structures (FIG. 6, row 2). This degradation phenomenon was typical of multiple formulations of filamentous PNC with even higher PLA content (FIGS. 8A-8H).

All publications, including any priority applications, cited in this specification are incorporated herein by reference. It will be appreciated that modifications can be made from the compositions and methods described herein without departing from the spirit of the invention embodied in the claims. Such modifications are intended to fall within the scope of the appended claims.

The invention claimed is:

1. A method of producing filamentous polymeric nanocarrier particles that encapsulate a biologically active protein, comprising:

(a) forming a primary emulsion using a freeze-thaw cycle of (i) an amphiphilic diblock copolymer, which has a molecular weight of about 10,000 to about 100,000 Da and comprises a hydrophobic polymer block conjugated to a hydrophilic polymer block, wherein said amphiphilic diblock copolymer comprises greater than 81% to about 95% by weight of said hydrophobic polymer block; and (ii) a biologically active protein having a molecular weight of up to or equal to about 300,000 Da;

(b) forming a secondary emulsion from said primary emulsion; and (c) recovering filamentous polymeric nanocarrier particles from the secondary emulsion, wherein said filamentous particles have a diameter of less than 70 nm and a length of from about 1 to about 50 microns, and encapsulate the biologically active protein and protect it from proteolysis.

2. The method according to claim 1, wherein said amphiphilic diblock copolymer has a molecular weight of about 10,000 to about 40,000 Da.

3. The method according to claim 1, further comprising conjugating an affinity moiety to the surface of said polymeric nanocarrier-encapsulated protein particles.

4. The method according to claim 1, wherein the hydrophilic polymer is a modified or unmodified polyethylene glycol.

5. The method according to claim 4, wherein the modified polyethylene glycol is selected from the group consisting of methoxypolyethylene glycol, amine modified polyethylene glycol, biotinylated polyethylene glycol, and an alkyne terminated polyethylene glycol.

6. The method according to claim 1, wherein the hydrophobic polymer is selected from the group consisting of a poly(lactic acid) polymer, and a polycaprolactone polymer.

7. The method according to claim 1, wherein said copolymer is permeable to substrates of said encapsulated protein.

8. A composition comprising polymeric nanocarrier particles that encapsulate a biologically active protein comprising:

(a) a biologically active protein having a molecular weight of up to or equal to about 300,000 Da;

(b) an amphiphilic diblock copolymer having a molecular weight of about 10,000 to about 100,000 Da and comprising a conjugate of a hydrophilic polymer block and a hydrophobic polymer block, wherein said total amphiphilic diblock copolymer comprises greater than 81% by weight of said hydrophobic polymer block; and wherein said composition is prepared by the method of claim 1 and comprises filamentous-shaped nanocarrier particles having a diameter of less than 70 nm and a length of from about 1 to about 50 microns, which encapsulate the biologically active protein and protect it from proteolysis.

9. The composition according to claim 8, wherein said amphiphilic diblock copolymer has a molecular weight of about 10,000 and 40,000 Da.

10. The composition according to claim 8, wherein said total amphiphilic diblock copolymer comprises between 82 to 95% by weight of said hydrophobic polymer block, and wherein said composition comprises primarily filamentous particles.

11. The composition according to claim 8, wherein the protein is an enzyme suitable for therapeutic or diagnostic use.

12. The composition according to claim 11, wherein said enzyme is an antioxidant enzyme, a xenobiotic detoxifying enzyme or a reporter enzyme.

13. The composition according to claim 8, wherein said polymeric nanocarrier-encapsulated protein particle comprises an affinity moiety on the outer surface of the nanocarrier.

14. The composition according to claim 8, wherein the hydrophilic polymer block is a polyethylene glycol and the hydrophobic polymer block is poly(lactic acid).

15. The composition according to claim 14, wherein the total amphiphilic diblock copolymer comprises 84% by weight of the poly(lactic acid).

16. A diagnostic or therapeutic method comprising administering to a mammalian subject or tissue thereof in vivo, ex vivo or in vitro, a composition of a claim 8.

17. A diagnostic or therapeutic method comprising administering to a mammalian subject or tissue thereof in vivo, ex vivo or in vitro, a composition comprising polymeric nanocarrier-encapsulated protein particles prepared by the method of claim 1.

* * * * *